(12) United States Patent
Holmes et al.

(10) Patent No.: US 8,673,983 B2
(45) Date of Patent: Mar. 18, 2014

(54) MELANINS SYNTHESIZED CHEMICALLY OR VIA ENZYME CATALYSIS

(75) Inventors: Earle W. Holmes, La Grange Park, IL (US); Kenneth D. Thompson, Loganville, WI (US)

(73) Assignee: Loyola University Chicago, Maywood, IL (US)

( * ) Notice: Subject to any disclaimer, the term of this patent is extended or adjusted under 35 U.S.C. 154(b) by 270 days.

(21) Appl. No.: 12/809,369

(22) PCT Filed: Dec. 22, 2008

(86) PCT No.: PCT/US2008/088004
§ 371 (c)(1),
(2), (4) Date: Jun. 18, 2010

(87) PCT Pub. No.: WO2009/082735
PCT Pub. Date: Jul. 2, 2009

(65) Prior Publication Data
US 2011/0230562 A1    Sep. 22, 2011

Related U.S. Application Data

(60) Provisional application No. 61/008,948, filed on Dec. 21, 2007.

(51) Int. Cl.
*A01N 33/18* (2006.01)
*A01N 33/24* (2006.01)
*A01N 43/16* (2006.01)

(52) U.S. Cl.
USPC .......................................... 514/728; 514/457

(58) Field of Classification Search
None
See application file for complete search history.

(56) References Cited

U.S. PATENT DOCUMENTS

| | | | |
|---|---|---|---|
| 5,057,325 A | | 10/1991 | Montefiori |
| 5,225,435 A * | | 7/1993 | Pawelek et al. ............... 514/415 |
| 5,628,799 A * | | 5/1997 | Wenke et al. ..................... 8/407 |
| 5,631,151 A * | | 5/1997 | della-Cioppa et al. ......... 435/133 |
| 5,814,495 A * | | 9/1998 | della-Cioppa et al. ......... 435/120 |
| 5,817,631 A | | 10/1998 | Berliner et al. |
| 5,837,505 A * | | 11/1998 | della-Cioppa et al. ......... 435/128 |
| 6,303,106 B1 | | 10/2001 | Banister et al. |
| 6,399,046 B1 * | | 6/2002 | Schonrock et al. ............. 424/59 |
| 6,440,691 B1 | | 8/2002 | Garger, Jr. et al. |
| 2007/0166255 A1* | | 7/2007 | Gupta ........................... 424/70.1 |

FOREIGN PATENT DOCUMENTS

WO    WO 2005021714 A2 *    3/2005

OTHER PUBLICATIONS

Vasyl M. Sava, Swen-Ming Yang, Meng-Yen Hong, Ping-Cheng Yang, Guewha Steven Huang; Isolation and characterization of melanic pigments derived from tea and tea polyphenols; Food Chemistry (2001) 73: 177-184.
Giuseppe Prota; Melanins and Melanogenesis; Academic Press, Inc., 1997.
Christine M.R. Clancy and John D. Simon; Ultrastructural Organization of Eumelanin from Sepia ofhcinalis Measured by Atomic Force Microscopy; Biochemistry 2001, 40, 13353-13360.
E. Holmes et al.; Phytomelanins as topical microbicides for the prevention of HSV and HIV infections, The FASEB Journal; 2005; A545-A545.
Chang-Peng Yang, Shuji Fujita, Koel Kohno, Akiko Kusubayashi, MD Ashrafuzzaman, and Nobuyuki Hayashi; Partial Purification and Characterization of Polyphenol Oxidase from Banana (*Musa sapientum* L.) Peel; J. Agric. Food Chem. 2001, 49, 1446-1449.
Yan Liu, Lian Hong, Kazumasa Wakamatsu, Shosuke Ito, Bhavin Adhyaru, Chi-Yuan Cheng, Clifford R. Bowers and John D. Simon; Comparison of Structural and Chemical Properties of Black and Red Human Hair Melanosomes; Photochemistry and Photobiology;; 2005, 81: 135-144.
Kenneth D. Thompson and Charles Drager; Antiviral Activity of Undaria pinnatifida against Herpes Simplex Virus; Phytotherapy Research; 18: 551-555, 2004.

* cited by examiner

*Primary Examiner* — Chris R Tate
*Assistant Examiner* — Douglas F White
(74) *Attorney, Agent, or Firm* — Hartman Global IP Law; Gary M. Hartman; Domenica N. S. Hartman

(57) ABSTRACT

The present invention provides an enzymatic and a chemical synthesis of melanins and novel melanins.

9 Claims, 32 Drawing Sheets

A. ES-CAM

B. nonenzymatic caffeic acid melanin

Retention Time (min)

A. ES-EM

B. nonenzymatic esculetin melanin

C1

C2

C5

C7

C10

C11

C12

C13

C14

C15

C16

C17

C18

C4

C9

C17

MELANINS SYNTHESIZED CHEMICALLY OR VIA ENZYME CATALYSIS

The present application is the national phase application of PCT Application No. PCT/US2008/088004, filed Dec. 22, 2008, which claims priority to U.S. Provisional Patent Application No. 61/008,948, filed Dec. 21, 2007, the entireties of both of which are hereby incorporated by references.

BACKGROUND

1. Technical Field

The present invention provides the chemical and enzyme-catalyzed synthesis of melanins. The synthesized melanins inhibit the binding of viruses to animal cells, prevent a virus from infecting the cells of its host, and prevent the spread of viral infections from person-to-person.

2. Background Information

Melanin is a general term for a group of high molecular weight black and brown pigments that arise from the oxidation and polymerization of polyphenols and aromatic amino acids (Prota, G., Melanins and Melanogenesis. 1992, San Diego: Academic Press, Inc. 1-290; Riley, P. A., Int. J. Biochem. Cell Biol. (1997) 29(11):1235-1239). Melanins are normal constituents of animal and plant tissues and are also present in many microorganisms. Melanins contribute to the coloration of the skin and hair of animals, the seeds, berries, flowers, and leaves of plants and to subcellular structures in certain bacteria and fungi. Despite many years of careful study, the precise chemical structures of natural melanins are virtually unknown. Structural elucidation has been hampered because of four main factors: the low molecular weight phenolic precursors of melanins are highly diverse; the oligomeric polyphenol units of natural melanins contain substituents that exist in several different oxidation states and as multiple structural isomers; melanins are typically isolated as heterogeneous mixtures; and melanins are resistant to analytical approaches based on chemical degradation. The potential for variability in melanin structure is so great that it may well be that no two melanin pigments are absolutely identical.

Melanins are typically identified by their unique physicochemical properties including their solubility characteristics, their tendency to aggregate in the presence of metal ions, their characteristic adsorption spectra in the UV and infrared regions, their ability to act as semi-conductors, their decolorization by strong oxidizing agents, their antioxidant and radioprotective properties, and their resistance to hydrolysis under strongly acidic and strongly basic conditions. Natural and enzymatically synthesized melanins exhibit strong absorption throughout the UV and visible regions. Published spectra are characterized by a monotonic increase in the absorbance with decreasing wavelengths with a barely detectable shoulder between 290 and 320 nm. The infrared spectra of melanins show absorption bands expected for an aromatic or a heteroaromatic system of OH, NH, and conjugated carbonyl groups. Recent analyses of a natural melanin from *Sepia officinalis* using a combination of scanning electron microscopy, atomic force microscopy, x-ray scattering, and mass spectrometry are consistent with the notion that natural melanins are comprised of small oligomeric units that aggregate to form stable filaments, particles (5-200 nm in diameter) and aggregates of the particles (Clancy, C. M. et al., Biochemistry (2001) 40 (44):13353-13360). These data suggest that the molecular constituents of melanin oligomers are made up of 4 to 8 monomer units. The oligomers have masses in the range of 500 to 1500 amu. Even after extensive investigations of this well-known natural melanin using the most sophisticated analytical approaches available, neither the precise structures of the melanin polymer nor that of the oligomeric constituents have been ascertained. Regardless of the source, it is unlikely that natural melanins are derived from unique well-defined building blocks.

The bulk of the scientific literature on melanin structure and function pertains to the mammalian melanins. Considerably less is known about the plant-derived melanins even though they are an abundant constituent of the biomass. The biosynthesis of plant melanins is catalyzed by a family of Type III polyketide synthetases (e.g., chalcone synthetase) which catalyze the first committed step in the synthesis of a large number of biologically important flavonoids and phytoalexins. The PKS III enzymes utilize a starter CoA-ester (e.g., p-coumaroyl-CoA) from the phenylpropanoid pathway and catalyze three sequential condensation reactions with an extender CoA-ester (e.g., malonylCoA). This is followed by a ring closure, and an aromatization to form chalcones (e.g., naringenin). Many different aromatic phenolics can be made by this mechanism depending on which polyketide synthetase is present and which of the many possible starter and extender CoA-esters are available for incorporation. The aromatic phenols and polyphenols that are the products of the polyketide pathway in a particular plant are oxidized to quinones by the enzyme polyphenol oxidase. The quinones are then joined together by free radical polymerization reactions to form oligomers that contain a mixture of quinone, hydroquinone, and semi-quinone functional groups. The oligomers associate to form stable, non-covalent complexes that take the form of particles, aggregates of particles, and fibers and exhibit the distinctive physical and chemical characteristics of the natural melanins.

Traditionally, melanins have been isolated from plants as heterologous, crude or purified preparations. Banister et al. (U.S. Pat. No. 6,303,106) describes the enzymatic production of melanins from phenolic compounds and an enzyme selected from tyrosinase, laccase and peroxidase. The produced melanins are used in the production of cosmetics.

The published literature concerning the use of plant-derived melanins as therapeutic agents is minimal. However, there have been a number of publications describing the isolation and characterization of melanins from fermented black tea (Sava, V.M. et al., Food Chemistry (2001) 73: 177-184) and from grapes (Novikov, D.A. et al., Radiats. Biol. Radioecol. (2001) 41(6):664- 670; Avramidis, N., et al., Arzneimittelforschung. (1998) 48(7): 764-771). These plant-derived melanins have been shown to possess a number of interesting pharmacological properties including immunomodulatory activity (A vramidis, 1998; Sava, V.M. et al., Food Research International (2001) 34: 337-343), photoprotective activity (Novikov, 2001), metal binding properties that make them useful as image enhancers in MRI (Hung, Y.C. et al., J. Ethnopharmacol. (2002) 79(1): 75-79), and the ability to protect animals from oxidant-induced tissue damage (Hung, Y.C. et al., Life Sci. (2003) 72(9): 1061-1071). Montefiori (U.S. Pat. No. 5,057,325) describes inhibition of human immunodeficiency virus (HIV) by chemically synthesized melanins, preferably melanins containing subunits of L-Dopa.

Synthetic melanins have been shown to have activity against HIV infections in in vitro cell culture models (Novikov, 2001; Garger, U.S. Pat. No. 6,440,691). The intrathecal administration of synthetic and natural melanins has been proposed as a treatment for certain neurodegenerative diseases, however evidence for their effectiveness has yet to be presented (Berliner, U.S. Pat. No. 5,817,631).

Crude and purified preparations of plant-derived melanins prevent viral infections by interfering with early steps in the infectious process namely the attachment of a virus to the epithelial cell membranes of a potential host and/or the fusion of the viral membrane with that of the host cell (Holmes, E. W. and Thompson, K. D., FASEB 1.19, (2005) Abstract No. 323.5, 2005). Host cells are protected from infection after only a brief period of melanin treatment and the protection afforded by the treatment persists for hours. Plant melanins are nontoxic to animal cells in vitro and cause no adverse effects following intravaginal administration in mice. Such properties make them ideal for the prevention of viral infections for which the portal of entry is the epithelium of the host.

Melanins have been chemically synthesized from hydroxyphenyl-containing precursors, mostly focused on catecholamines and catecholamine derivatives (e.g. DOPA, Dopamine, etc). Quinones are generated at basic pH spontaneously, followed by polymerization. However, the resulting polymers are often found to be poorly soluble in biocompatible solvents, and hence, are not likely to be useful as pharmaceuticals. Another disadvantage of many of the synthetic polymers of hydroxyphenyl compounds is that data documenting the scopes and potencies of their antimicrobial activities is either limited or unavailable.

It would be desirable to synthetically produce melanins in high yields under reproducible conditions. Further, it would be desirable to produce novel melanins, especially water-soluble melanins, with antiviral activity.

BRIEF SUMMARY

The present invention provides a method for producing a melanin comprising the step of: (a) contacting an oxidase and a phenolic substrate containing at least two hydroxyl groups for a time sufficient to produce a melanin. The method can optionally further comprise any of the following steps: (b) inactivating the oxidase, (c) precipitating the melanin, and/or (d) purifying the melanin.

The present invention further provides a melanin produced by the step of (a) contacting (1) an oxidase and (2) at least one phenolic substrate with at least two hydroxyl groups for a time sufficient to produce a melanin. The method of the present invention can be used to produce novel homologous (single PPO substrate) and heterologous (two or more PPO substrates) melanins, including enzymatically synthesized melanins comprising bicyclic dihydroxyphenolic monomers.

The present disclosure also provides a method for the chemical synthesis of a melanin. The method comprises the step of: (a) contacting a phenolic substrate and a catalyst for a time sufficient to produce a melanin. The method can optionally further comprise the step of: (b) purifying the melanin. The substrate contains two or more aromatic hydroxyl-groups.

The present invention includes novel enzymatically and chemically synthesized melanins, including those prepared from cinnamic acid and those prepared from coumarin. The melanins of the present invention are typically water soluble.

The present invention further provides antiviral compositions, especially compositions suitable for intravaginal, intrarectal, or topical use.

The enzymatically and chemically synthesized melanins of the present invention can be used to prevent infections, especially those that are caused by enveloped viruses, and those which are sexually transmitted.

DETAILED DESCRIPTION OF THE PREFERRED EMBODIMENTS

Enzymatic Methods

Figure 1:
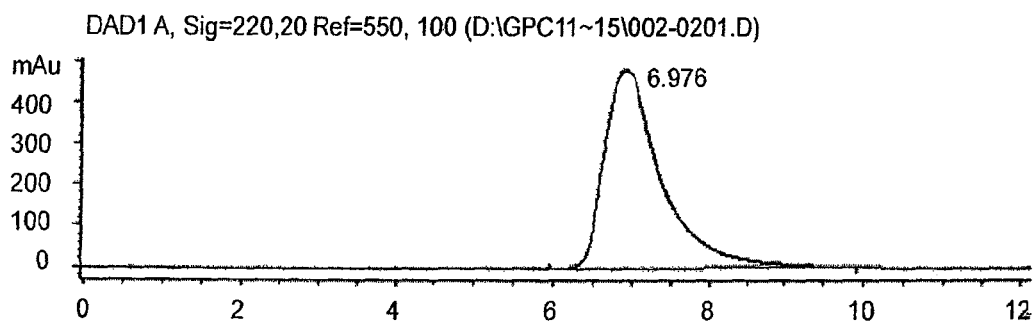
FIG. 1 is a HPLC-GPC chromatogram of enzymatically synthesized caffeic acid melanin ("ES-CAM") and non-enzymatically synthesized caffeic acid melanin. ES-CAM prepared by the enzymatic process described in this disclosure (A) and caffeic acid melanin prepared by a nonenzymatic synthesis procedure (B) were analyzed by HPLC on a column of BioSep SEC-S2000. The mobile phase, 0.05 M sodium borate, pH 8.6, was pumped at a flow rate of 0.75 mL/min. Compounds in the effluent were detected by their absorbances at 220 nm using a diode array detector. The column was calibrated with polymer standards of known molecular weights to enable the estimation of molecular weight based on retention time.
Figure 1:
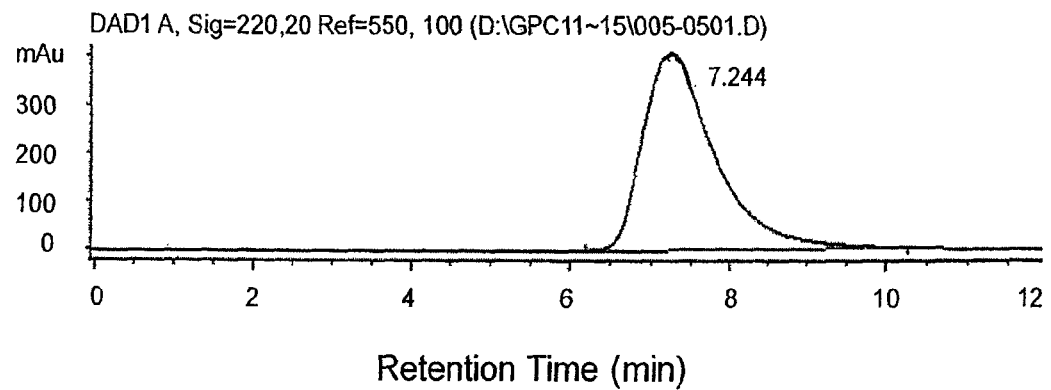

The present invention provides a method for producing a melanin comprising the step of: (a) contacting a polyphenol oxidase (PPO) and a pyrocatechol substrate for a time sufficient to produce a melanin. The method can optionally further comprise any of the following steps: (b) inactivating the oxidase, (c) precipitating the melanin, and/or (d) purifying the melanin.

Typically, the PPO and pyrocatechol substrate are contacted for at least 6 hours, preferably at least 12 hours, more preferably at least 24 hours. The enzymatic reaction is typically conducted in aqueous media, at a neutral pH, and at least at room temperature.

The reaction can be terminated by inactivating the PPO either chemically, by altering the pH of the reaction (for example, by adding base or acid), or physically (by heating or cooling the reaction).

Melanin can be purified from the reaction mixture by precipitation (as described below in the examples), centrifugation, chromatography and other well known methods.

Polyphenol Oxidase

Any PPO can be used in accordance with the present invention. PPOs can be isolated from mammalian, plant and fungal sources. Exemplary PPOs include banana and mushroom PPO enzyme and tyrosinases from various sources. Preferably, mushroom PPO enzyme is used. Any activity of enzyme can be used.

PPO Substrates

The substrates of the present invention are pyrocatechol substrates. In some cases, tri-hydroxyl benzene substrates can be used.

The pyrocatechol substrates of the present invention typically have one of the following cores:

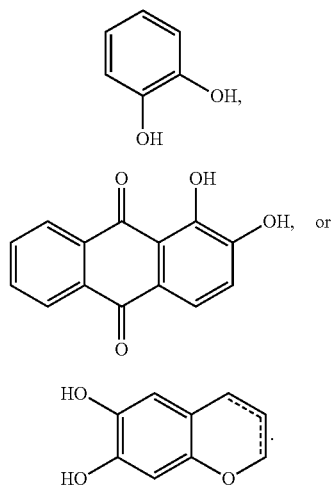

These cores can have one or more substituents including hydroxyl, amino, thiol, carbonyl, unsubstituted or substituted alkyl, unsubstituted or substituted-8-carbocyclyl, unsubstituted or substituted aryl, unsubstituted or substituted heterocyclyl, and unsubstituted or substituted heteroaryl. In formula (III), one or none of the dashed lines can be a double bond. Other cores can also be used.

When more than one substrate is used, at least one substrate must be a pyrocatechol substrate; however the other substrate(s) may be a phenolic substrate or any other molecule containing an electron-rich center or functional group, for example, a conjugated double bond, an amino group, or a sulfhydryl group. By combining mixtures of substrates, novel melanins can be obtained. In one embodiment, the pyrocatechol substrate is a bicyclic compound such as esculetin, dapthnetin, catechin, baicalein or alizarin. In another embodiment, the pyrocatechol substrate is a monocyclic compound.

Exemplary pyrocatechol substrates useful in the present invention are shown below in Table 1. Exemplary phenolic substrates include dopamine, L-DOPA, catechin hydrate, pyrocatechol, protocatechuric acid, serotonin, DOPAC, deoxyepinephrine, isoproterenol, norepinephrine, epinephrine bitartrate, baicalein, 2,3-dihydroxybenzoic acid, esculetin, 2,3,4-trihydroxybenzoic acid, quercetin, gallic acid, 2,3, 4-trihydroxybenzaldehyde, alizarin, 2,3-dihydroxynapthalene, pyrogallol, caffeic acid, nordihydroguaiaretic acid, daphnetin, phenol red, and 4-methyl daphnetin.

In one embodiment, the phenolic substrate is selected from the group consisting of dopamine, L-DOPA, caffeic acid, protocatechuric acid, DOPAC, deoxyepinephrine, gallic acid or pyrogallol.

In one embodiment, an initial amount of PPO substrate can be coupled to a solid phase. Thereafter the polymerization reaction can be conducted in solution by exposing the solid phase to enzyme and further PPO substrate. In this way, the formed melanin can be easily manipulated and isolated.

Novel Enzymatically Synthesized Melanins

Enzymatically synthesized melanins prepared by this invention are generally found to be soluble in aqueous solutions at pH's that are within the physiological range for humans and other animal species.

Enzymatically synthesized melanins prepared by this invention typically are composed of 50 to 200 substrate monomers. These melanins are typically aggregates of oligomers with different degrees of polymerization.

In one preferred embodiment, the enzymatically synthesized melanin is prepared from the phenolic substrate caffeic acid. Such melanins are water-soluble, and are composed of oligomers with molecular weights in the range of approximately 1.2 to 5.4 kDa which, in turn, aggregate in aqueous solution to form complexes with a number average molecular weight of approximately 19.7 kDa.

In another preferred embodiment, the enzymatically synthesized melanin is prepared from the phenolic substrate esculetin. Such melanins are water-soluble and are composed of oligomers with molecular weights in the range of approximately 1.0 to 5.0 kDa which, in turn, aggregate in aqueous solution to form complexes with a number average molecular weight of approximately 15.4 kDa.

Enzymatically synthesized melanins prepared according to this invention are water soluble polymers of sufficient molecular weight to be nondialyzable through standard dialysis membranes with molecular weight cutoffs in the range of 10 to 13 kDa. The enzymatically synthesized melanins precipitate at pH's of less than 4.5. These enzymatically synthesized melanins typically have ultraviolet absorbance spectra that are characterized by steep increases in absorbance as the excitation wavelength decreases from 300 to 200 nm. Such melanins typically have FTIR spectra that demonstrate strong absorption bands in at least some of the following regions: at approximately 3400 $cm^{-1}$; in the 1600 to 1700 $cm^{-1}$ range; in the 1500 to 1600 $cm^{-1}$ range; in the 1360 to 1410 $cm^{-1}$; and in the 1220 to 1280 $cm^{-1}$ range. Enzymatically synthesized melanins prepared according to this invention typically have positive ion MALDI TOF mass spectra that show partially resolved distributions of singly-charged pseudo-molecular ions between approximately 1000 and 5400 m/z units. These results show that enzymatically synthesized melanins are heteropolymers composed of lower molecular weight oligomers of different degrees of polymerization. The mass spectra further suggest that the higher molecular weight oligomers contain multiple intra-chain ring closures that produce extended polynuclear (i.e. graphite-like) structures.

Chemical Methods

The present disclosure also provides a method for the chemical synthesis of a melanin. The method comprises the step of: (a) contacting a phenolic substrate and a catalyst for a time sufficient to produce a melanin. The method can optionally further comprise the step of: (b) purifying the melanin. The substrate contains two or more aromatic hydroxyl-groups.

The reaction is typically conducted in aqueous media, at a basic pH and at an elevated temperature. The resulting melanin can be purified from the reaction mixture by dialysis, chromatography and other well know methods.

The examples of the catalyst include iron, cobalt and nickel complexes. The preferred example is N,N'-bis(salicylidene) ethylenediaminocobalt (II) (salcomine).

Examplary substrates include pyrogallol, quercetin dihydrate, daphnetin, 2,3-dihydroxynapthalene, 3,4 dihydroxybenzoic acid (protocatechuric acid), 6,7-dihydroxy-4-coumarinyl acetic acid, baicalein, gallic acid, 3,4-dihydroxyphenylacetic acid, esculetin, caffeic acid, catechin, nordihydroquaiuretic acid, baicalein hydrate, 2,3,4-trihydroxybenzoic acid, epinephrine (bitartrate), epinine (2-deoxy norepinephrine), and 2,3,4-trihydroxybenzaldehyde.

In the disclosed embodiments, 18 homopolymers were synthesized using the 18 different precursors, listed in Table 4. The chemically synthesized polymers are highly water-soluble compared to catecholamine-derived synthetic melanins and natural melanins derived from Sepia or human hair. The products are stable as dry powders (possibly indefinitely). The synthetic polymers are likely to be structurally unique polymers that have not been previously described, and may also serve as lead compounds for the development of derivatives that may have additional unique and useful activities or applications. Synthetic melanins can be used as components of multi-agent prophylaxis or treatment regimens in which multiple mechanisms of microbial infection are simultaneously targeted. The melanins made using this process are active against many different viruses including HIV, HSV 1, and HSV 2, CMV, VZV, Influenzas A and B, SARS, Vaccinia, Cowpox, RSV, Tacaribe, Dengue, and Rift Valley Fever, and have low toxicities toward animal cells. They may be used as for the prevention of diseases such as herpes and AIDS in humans as well as diseases caused by a number of different enveloped viruses that infect insects, crustaceans, fish, cattle, poultry and other animal species.

This method represents the first demonstration of the generalizability of a rational chemical synthetic process for the production of synthetic melanins from a wide variety of dihydroxyphenol-containing compounds. The combination of a buffer regulated, moderately basic pH, a cobalt complex (such as salcomine), and molecular oxygen enables the formation of reactive para-quinones, in a process for the synthesis. The synthetic approach may be used to prepare homo- or hetero-polymers from many different hydroxyphenol-containing substrates, and also makes it possible to incorporate mono-hydroxylphenols into synthetic homo- or hetero-polymers analogs. The process is scalable and provides reasonable yields of products.

Compositions

Melanins of the present invention can be formulated into compositions by the addition of a pharmaceutically acceptable carrier. Suitable pharmaceutical carriers are described in Remington's Pharmaceutical Sciences, Mack Publishing Company, a standard reference text in this field.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of the invention may be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated (for example, as described in Finnin and Morgan, J. Pharm. Sci., 88(10): 955-958 (October 1999)). Other means of topical administration include delivery by iontophoresis, electroporation, phonophoresis, sonophoresis and microneedle or needle-free injection.

The melanin can be administered orally in solid dosage forms, such as lozenges, capsules, tablets, and powders, or in liquid dosage forms, such as elixirs, syrups, mouthwashes and suspensions. It can also be administered parenterally, in sterile liquid dosage forms. The melanin can also be administered intranasally (nose drops) or by inhalation of a drug powder mist. Other dosage forms are potentially possible such as, administration transdermally, via patch mechanism or ointment. The melanin can be administered employing a sustained or delayed release delivery system or an immediate release delivery system.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the melanin, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the melanin in a flavor, usually sucrose and acacia or tragacanth, as well as pastilles comprising the melanin in an inert base, such as gelatin and glycerin, or sucrose and acadia, emulsions, and gels containing, in addition to the melanin, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty acid alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-aminopropionates, and 2-alkylimidazoline quaternary ammonium salts, and (e) mixtures thereof.

The parenteral formulations typically contain from about 0.5% to about 25% by weight of the melanin in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the melanins and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

The melanins of the present invention can be formulated as:

1. Coatings on medical grade substrates, for example, dressings, packings, meshes, films, filtering surfaces, filters, infusers, fibers such as dental floss or sutures, containers or vials, from materials composed of, for example, polyethylene, high density polyethylene, polyvinylchloride, latex, silicone, cotton, rayon, polyester, nylon, cellulose, acetate, carboxymethylcellulose, alginate, chitin, chitosan and hydro fibres;

2. Powders or as coatings on biocompatible substrates in powder form, preferably on hydrocolloids, bioabsorbable and/or hygroscopic substrates such as: synthetic bioabsorbable polymers (for example polyesters/polylactones such as polymers of polyglycolic acid, glycolide, lactic acid, lactide, dioxanone, trimethylene carbonate etc., polyanhydrides, polyesteramides, polyorthooesters, polyphosphazenes, and copolymers of these and related polymers or monomers) or naturally derived polymers (for example, proteins such as albumin, fibrin, collagen, elastin; polysaccharides such as chitosan, alginates, hyaluronic acid; acellular matrix materials such as small intestinal submucosa; and biosynthetic polyesters such as 3-hydroxybutyrate polymers);

3. Occlusions or hydrated dressings, in which the dressing is impregnated with a powder or solution, or is used with a topical formulation, with such dressings for example as hydrocolloids, hydrogels, polyethylene, polyurethane, polvinylidine, siloxane or silicone dressings;

4. Gels, formulated with powders or solutions of the melanins with such materials as hydrocolloid powders such as carboxymethylcellulose, alginate, chitin, chitosan and hydro fibres, together with such ingredients as preservatives, pectin and viscosity enhancers;

5. Creams, lotions, pastes, foams and ointments formulated with powders or solutions of the melanins, for example as emulsions or with drying emollients;

6. Liquids, formulated as solutions, dispersions, or suspensions, by dissolving coatings or powders of the melanins, for example as topical solutions, aerosols, mists, sprays, drops, infusions and instillation solutions for body cavities and tubes such as the bladder, prostate, perineal, pleural, intestinal and alimentary canal;

7. Formulations suitable for administration to the nasal membranes, the oral cavity or to the gastrointestinal tract, formulated with powders or liquids of the melanins in such forms as lozenges, toothpastes, gels, powders, coated dental implants, dental floss or tape, chewing gum, wafers, mouth washes or rinses, drops, sprays, elixirs, syrups, tablets, or capsules;

8. Formulations suitable for vaginal or rectal administration formulated with powders or liquids of the melanin formulated in or coated on such forms as suppositories, dressings, packings, condoms, tampons, diaphragms, creams, gels, ointments, pastes, foams, sprays, and solutions for retention enemas or instillations. Transvaginal drug delivery is a well known means of administering drugs to a female (Woolfson, A. D., Malcolm, R. K. and Gallagher, R. (2000) Critical Reviews in Therapeutic Drug Carrier Systems, 17:509 555). Known transvaginal drug delivery systems include mucoadhesive gels and hydrogels (such as weakly crosslinked polymers which are able to swell in contact with water and spread onto the surface of mucus); vaginal tablets (formulated with mucoadhesive polymers in order to increase intravaginal residence time); vaginal pessaries and suppositories (such as natural gums, fatty acids, alum and rock salts); microspheres for the delivery of peptide and protein drugs; and intravaginal rings (torus-shaped polymeric devices designed to release one or more incorporated substances in a controlled fashion). Additionally, formulations suitable for rectal administration may be presented as suppositories by mixing with a variety of bases such as emulsifying bases or water-soluble bases.

Methods of Use

Melanins of the present invention can be used for either prevention or treatment of viral diseases.

"HIV disease" refers to a well recognized constellation of signs and symptoms (including the development of opportunistic infections) in persons who are infected by an HIV virus, as determined by antibody or western blot studies. Laboratory findings associated with this disease are a progressive decline in T-helper cells.

The dose administered to an animal, particularly a human, in the context of the present invention should be sufficient to effect a therapeutic response in the animal over a reasonable time frame.

One skilled in the art will recognize that dosage will depend upon a variety of factors including a condition of the animal, the body weight of the animal, the nature and extent of the symptoms, the kind of concurrent treatment, the frequency of treatment, etc. The size of the dose also will be determined by the route, timing and frequency of administration as well as the existence, nature, and extent of any adverse side effects that might accompany the administration of the compound and the desired physiological effect.

A daily dosage of melanin can be expected to be about 0.001 to 1000 milligrams (mg) per kilogram (kg) of body weight, with the preferred dose being 0.1 to about 30 mg/kg. Dosage forms (compositions suitable for administration) contain from about 1 mg to about 500 mg of melanin per unit. In these pharmaceutical compositions, the melanin will ordinarily be present in an amount of about 0.5-95% weight based on the total weight of the composition.

The melanins of the present invention can be used in the treatment of a variety of viral diseases including herpes viruses (such as cytomegalovirus (CMV), HSV-I, HSV-2, VZV, EBV), HPV, lentiviruses (such as HIV-1, HIV-2), simian immunodeficiency virus (SIV), feline immunodeficiency virus (FIV), influenza (including avian influenza viruses and human influenza viruses) and para-influenza, Human T-lymphotropic viruses (such as HTL V-1, HTL V-2), RSV, Tacaribe, Dengue, Rift Valley Fever Virus, spumavirus (human foamy virus) and feline infectious leukemia, members of the Retrovirus, Rhabdovirus, Arbovirus, Orthomyxovirus, Paramyxovirus, Filovirus, Alphavirus, Herpesvirus, Hepadnavirus, Poxvirus families, Noroviruses, Picornaviruses, as well as diseases caused by intracellular pathogens such as *Listeria, Mycobacteria, Brucella, Salmonella, Rickettsia, Trophyrema, Cryptococcus, Cryptosporidium, Microsporidium,* and bacterial toxins such as that of *C. difficile.*

The melanins of the present invention can be used in the treatment of other viral diseases including amyloidogenic diseases (including Alzheimer's and multiple myeloma), Hepatitis B, and prion diseases (including kuru, Creutzfeldt-Jakob Disease (CJD), Gerstmann-Strassler-Scheinker Disease (GSS), and fatal familial insomnia (FFI), scrapie and bovine spongiform encephalopathy (BSE)); genital warts; common warts; plantar warts; Hepatitis C; molluscum contagiosum; variola, particularly variola major; VZV; rhinovirus; adenovirus; coronavirus; intraepithelial neoplasias such as cervical intraepithelial neoplasia; human papillomavirus (HPV) and associated neoplasias; fungal diseases, e.g. *candida, aspergillus,* and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; and parasitic diseases, e.g. pneumocystis camii, cryptosporidiosis, histoplasmosis, toxoplasmosis, trypanosome infection, and leishmaniasis. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of Keloid formation after surgery and other types of post-surgical scars; and bacterial infections, e.g., *tuberculosis,* and *mycobacterium avium.* In addition, these compounds could enhance or stimulate the healing of wounds, including chronic wounds.

The melanins of the present invention can be used in the treatment of viral diseases that affect cattle, fowl, cultured marine species, pets, and natural populations of wild animals. These diseases include herpes virus infections in cows, goats, pigs, sheep, ducks, chickens and turkeys and catfish horses, cats, and dogs, Marek's disease, avian leukosis, and viral hemorrhagic septicemia.

The present invention includes prevention and treatment for HIV disease and associated diseases, especially those caused by enveloped viruses, in a subject such as an animal, for example a human. The method includes administering the melanins of the present invention, or a combination of the compound and one or more other pharmaceutical agents, to the subject in a pharmaceutically compatible carrier and in an amount effective to inhibit the development or progression of HIV disease. Although the treatment can be used prophylactically in any patient in a demographic group at significant risk for such diseases, subjects can also be selected using more specific criteria, such as a definitive diagnosis of the condition.

The melanins of the present invention are ideally administered as soon as possible before potential or after actual exposure to HIV infection. For example, once HIV infection has been confirmed by laboratory tests, a therapeutically effective amount of the melanin is administered.

Combination Therapy

The present invention also includes combinations of melanins with one or more agents useful in the treatment of HIV disease. For example, the melanins of this invention may be administered, whether before or after exposure to the virus, in combination with effective doses of other anti-virals, immunomodulators, anti-infectives, or vaccines. The term "administration" refers to both concurrent and sequential administration of the active agents.

Example of antivirals that can be used in combination with the melanins of the invention are: AL-721 (from Ethigen of Los Angeles, Calif.), recombinant human interferon beta (from Triton Biosciences of Alameda, Calif.), Acemannan (from Carrington Labs of Irving, Tex.), ganciclovir (from Syntex of Palo alto, Calif.), didehydrodeoxythymidine or d4T (from Bristol-Myers-Squibb), ELIO (from Elan Corp. of Gainesville, Ga.), dideoxycytidine or ddC (from Hoffman-LaRoche), Novapren (from Novaferon labs, Inc. of Akron, Ohio), zidovudine or AZT (from Burroughs Wellcome), ribaririn (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

The combination therapies are of course not limited to the lists provided in these examples, but includes any composition for the treatment of HIV disease (including treatment of AIDS).

Examples of immuno-modulators that can be used in combination with the melanins of the invention are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, and TNF (Genentech).

Examples of some anti-infectives with which the melanins can be used include clindamycin with primaquine (from Upjohn, for the treatment of pneumocystis pneumonia), fluconazlone (from Pfizer for the treatment of cryptococcal meningitis or candidiasis), nystatin, pentamidine, trimethaprimsulfamethoxazole, and many others.

EXAMPLES

Banana PPO enzyme was purified from banana skins by a previously published method (C. P. Yang, et al. (2001) J. Agric. Food Chem. 49: 1446-1449). Small-scale test reactions were carried out by mixing 5 µL of enzyme solution (66 units of catechol oxidase activity) and 2.5 mg of a phenolic test substrate in 2.5 ml of 0.2 M sodium/potassium phosphate buffer, pH 7.0. A blank reaction mixture containing all of the components except the PPO enzyme was prepared for each test substrate so that enzyme-mediated pigment formation could be distinguished from the non-enzymatic oxidation of the substrate. The test mixtures and their corresponding blanks were covered with Parafilm and incubated at 23° C. for 24 hours. The antiviral activity of each test and blank reaction mixture was determined by measuring its ability to inhibit the infection of cultured human foreskin fibroblasts by HSV 1. A PPO product was considered to be soluble in aqueous solution when enzymatically formed pigment in the test reaction was present in a clear supernatant at the end of the incubation period. Base-soluble products were pigments that presented as cloudy or turbid suspensions or as precipitates at the end of the incubation, but were transformed into clear solutions by the dropwise addition of 0.1 N NaOH. Table 1 shows the results of our test of 35 potential melanogenic substrates of the PPO enzyme (E.C. 1.10.3.1) from banana (*Musa sapientum*) skin.

TABLE 1

Physical Properties and Antiviral Activities of Melanins Prepared by Enzymatic Process.

| Substrate Common Name | Substrate Chemical Name | PPO Substrate | Solubility[1,2] | Anti-HSV-1 titer[3] |
|---|---|---|---|---|
| Dopamine | 3,4-dihydroxyphenylamine | Y | b | 20 |
| L-DOPA | 3-(3,4-dihydroxyphenyl)-L-alanine | Y | b | 80 |
| L-tryptophan | A-aminoindole-3-propionic acid | N | — | — |
| Catechin Hydrate | 2-(3,4-dihydroxyphenyl)-3,4-dihydro-2H-1-benzopyran-3,5,7-triol | Y | b | 20 |
| Pyrocatechol | 1,2-benzenediol | Y | b | toxic |
| Chlorogenic acid | 3-(3,4-dihydroxy-cinnamovljquinic acid | N | — | — |
| p-Coumaric acid | 4-hydroxycinnamic acid | N | — | — |
| Protocatechuric acid | 3,4-dihydroxybenzoic acid | Y | aq | 160 |
| Naringenin | 4',5,7-trihydroxyflavanone | N | — | — |
| Tryptamine | 3-(2-aminoethyl)indole | N | — | — |
| Serotonin | 5-hydroxytryptamine | Y | aq | toxic |
| Syringic acid | 4-hydroxy-3,5-dimethoxybenzoic acid | N | — | — |
| Vanillic acid | 4-hydroxy-3-methoxy-benzoic acid | N | — | — |
| Kynurenic acid | 4-hydroxy-2-quinolinecarboxylic acid | N | — | — |
| Homovanillic acid | 4-hydroxy-3-methoxy-phenylacetic acid | N | — | — |
| DOPAC | 3,4-dihydroxyphenylacetic acid | Y | aq | 160 |
| Deoxy-epinephrine | 3,4-dihydroxy-phenylethylamine | Y | b | 80 |
| Isoproterenol | 3,4-dihydroxy-alpha-[(isopropyl amino)methyl]-benzyl alcohol | Y | aq | toxic |
| Norepinephrine | 2-amino-I-(3,4-dihydroxyphenyl)ethanol | Y | b | toxic |
| Epinephrine bitartrate | 3,4-dihydroxy-1-[I-hydroxy-2-(methylamino)-ethvllbenzene | Y | aq | 80 |
| Resorcinol | 1,3-benzenediol | N | — | — |
| L-Tyrosine | B-(p-hydroxyphenyl)-alanine | N | — | — |
| O-Tyrosine | B-(p-hydroxyphenyl)-alanine | N | — | — |
| | 3-nitro-L-tyrosine | N | — | — |
| Baicalein | 5,6,7 trihydroxyflavanone | Y | b | 10 |
| | 2,3 dihydroxybenzoic acid | y/n | aq | <10 |
| Esculetin | 6,7 Dihydroxvcoumarin | Y | aq | 320 |
| | 2,3,4-trihydroxybenzoic acid | Y | aq | 20 |
| β-resorcylic acid | 2,4-dihydroxybenzoic acid | N | — | — |
| Quercetin | 2-(3,4-dihydroxyphenyl)-3,5,7-trihydroxy-4H-1-benzopyran-4-one | y/n | b | toxic |
| Gallic acid | 3,4,5-trihydroxybenzoic acid | Y | aq | 80 |
| | 2,3,4-trihydroxybe~dehyde | Y | aq | <10 |
| Alizarin | 1,2-dihydroxy-anthraquinone | Y | b | toxic |
| | 2,3-dihydroxynapthalene | Y | aq | 40 |
| Pyrogallol | 1,2,3-trihydroxvbenzene | Y | aq | 80 |
| Caffeic acid | 3,4-dihydroxycinnamic acid | Y | aq | 160 |

[1] the test reaction mixture became colored over time and its color intensity exceeded that which developed in the blank reaction mixture.
[2] aq: product soluble in 0.2M phosphate buffer at pH 7.0; b: product required the addition of strong base to achieve solubility.
[3] titer values are directly proportional to antiviral potency. These results are relative values and were obtained by making a starting dilution of 1:10 from the synthetic preparation and then preparing serial two-fold dilutions through 1:1280. Therefore, the least amount of activity was <1:10 and the higher the number the greater the activity. The antiviral titer was determined in an in situ ELISA using HSV-1. With each ELISA plate, there was a column of eight wells that have cells but do not have either virus or drug and were used as the negative controls. There was also a column of eight wells with cells infected with HSV-1 but without drug that was used as the positive control. "Toxic" means that the compound was toxic to the cells so that it was not possible to determine any antiviral activity. The toxic effect of compounds to the cells makes the cells appear shrunken, crenated, pycnotic, and irregularly shaped. The cytopathic effect of HSV-1 causes the cells to be enlarged and round.

The results showed that dihydroxyphenyl containing molecules are generally melanogenic at neutral pH in this enzyme-catalyzed process, but that many of the substrates yielded products that were not soluble in aqueous solutions at neutral pH. Furthermore, some of the soluble melanins were toxic to the cultured human cells that were used to test for antiviral activity. Among the soluble, nontoxic melanins, 14 inhibited the infection of cultured human cells by HSV-1. Among this group of compounds, the most potent melanins were produced from benzoic acid (e.g. protocatechuric acid), cinnamic acid (e.g. caffeic acid) and dihydroxycoumarin (e.g. esculetin) substrates.

The enzyme catalyzed synthesis of antiviral melanins was further tested using a purified PPO (I.U.B.: 1.14.18.1) from *Agaricas bisporus* (mushroom) as the catalyst. This enzyme was tested for its ability to produce antiviral melanins from 13 dihydroxy phenyl-containing substrates. For this test, 2.0 mg of substrate was added to 1 ml of 0.1 M potassium phosphate, pH 7.0 that contained 0.8 mg (22 catechol oxidase units) of mushroom PPO. Blank reaction mixes containing all ingredients except for the PPO were simultaneously evaluated. Despite the fact that 10 of the 13 substrates were only sparingly soluble, the suspensions of these substrates in the test and blank reaction mixtures were capped with parafilm and incubated in a block heater at 30° centigrade for 45 hours. The final pigmented solutions were centrifuged at 10,000 g and the supernatants were placed in a boiling bath for 20 minutes to inactivate the enzyme. The soluble supernatants containing enzymatically synthesized melanins were active against HSV-1 at the inhibitory titers shown in Table 2.

TABLE 2

Physical Properties and Antiviral Activities of Melanins Prepared by Enzymatic Process.

| Substrate | Soluble Substrate[1] | Anti-HSV 1 Titer[2] | Toxicity | Soluble Product[3] |
|---|---|---|---|---|
| Phenol Red | n | <10 | N | y |
| Baicalein | n | <10 | N | y |
| Quercetin | n | 320 | N | y |
| 2,3 Dihydroxynapthalene | n | 80 | Y | y |
| Nordihydroguaiuretic acid | n | 10 | N | y |
| Gallic acid | n | 160 | Y | y |
| Caffeic acid | y | 1280 | N | y |
| Alizarin | n | <10 | N | y |
| DOPAC | y | 320 | N | y |
| Pyrogallol | n | 160 | Y | y |
| Catechin | n | 40 | N | n |
| Protocatechuric acid | y | 640 | N | y |
| Esculetin | n | 640 | N | y |
| Dapthnetin | n | 320 | N | y |

[1] y: substrate completely soluble in reaction mixture; n: substrate present in reaction mixture as a saturated solution.
[2] Titer was directly proportional to anti-viral potency. See footnote 3 in Table 1.
[3] n: product formed a visible precipitate when diluted 1/10 or 1/20 in cell culture media All but one of these enzymatically synthesized melanin products was soluble in aqueous buffer at a neutral pH. Based on initial studies such as these, 2 substrates, caffeic acid and esculetin, were selected for the purpose of demonstrating a general, scalable process for the production of enzymatically synthesized melanins from precursors containing dihydroxyphenyl substituents.

Process for the Production of Caffeic Acid Melanin (ES-CAM).

150 mg of caffeic acid (3,4-dihydroxy cinnamic acid, Sigma Aldrich, Milwaukee, Wis., catalog No. D11, 080-9) was added to a 150 mL Erlenmeyer flask containing 60 mL of 0.1 M potassium phosphate buffer, pH 7.

The mixture was stirred for 10 minutes at 23° C. to provide a solution with the pH of 6.73. The pH was adjusted to 7.0 with dilute sodium hydroxide. 60 mg polyphenol oxidase (PPO) (23 units per mg catechol oxidase activity, Worthington Biochemicals Corp. Lakewood N.J., Catalog No. TY) was added and swirled in the flask to dissolve the enzyme. The flask was covered with parafilm and incubated in a block heater for 48 hours at 40° C. The flask was then placed in a boiling water bath for 20 minutes to inactivate and denature the PPO. The mixture was cooled and the pH adjusted to pH 3.5 by adding HCl. The flask was allowed to stand overnight under refrigeration to precipitate the enzymatically synthesized melanin product. This suspension was centrifuged, and the melanin pellet washed 3 times with 24 mL of 0.01 N HCl. The washed pellet was dissolved in 16 ml of 0.2 M sodium bicarbonate. This solution was dialyzed in SpectralPor 4 cellophane dialysis tubing (10-14 kDa MWCO, Spectrum Laboratories Inc., Rancho Dominguez, Calif.) against 4×4 L changes of deionized water. The retentate was lyophilized. Enzymatically synthesized melanin product was recovered as a dark brown powder with a dry weight of 128 mg (85% yield).

Process for the Production of Esculetin Melanin (ES-EM).

150 mg of esculetin (6,7-dihydroxycoumarin (Sigma-Aldrich, Milwaukee, Wis., catalog No. 24,6573) was added to 60 ml of 0.1 M potassium phosphate buffer pH 7 in an Erlenmeyer flask and mixed for 10 minutes at 23° C. 60 mg of mushroom PPO was added to this saturated solution and gently swirled in the flask to dissolve the enzyme. The flask was covered with parafilm and incubated at 40° C. for 144 hours. The flask was placed in a boiling water bath, and the enzymatically synthesized melanin product, ES-EM, was isolated by acid precipitation, washing, dialysis, and lyophilization as described for ES-CAM. ES-EM was recovered as an amber colored powder with a dry weight of 116 mg (77% yield).

Physical Properties of Enzymatically Synthesized Melanins Prepared by this Invention.

Figure 3:
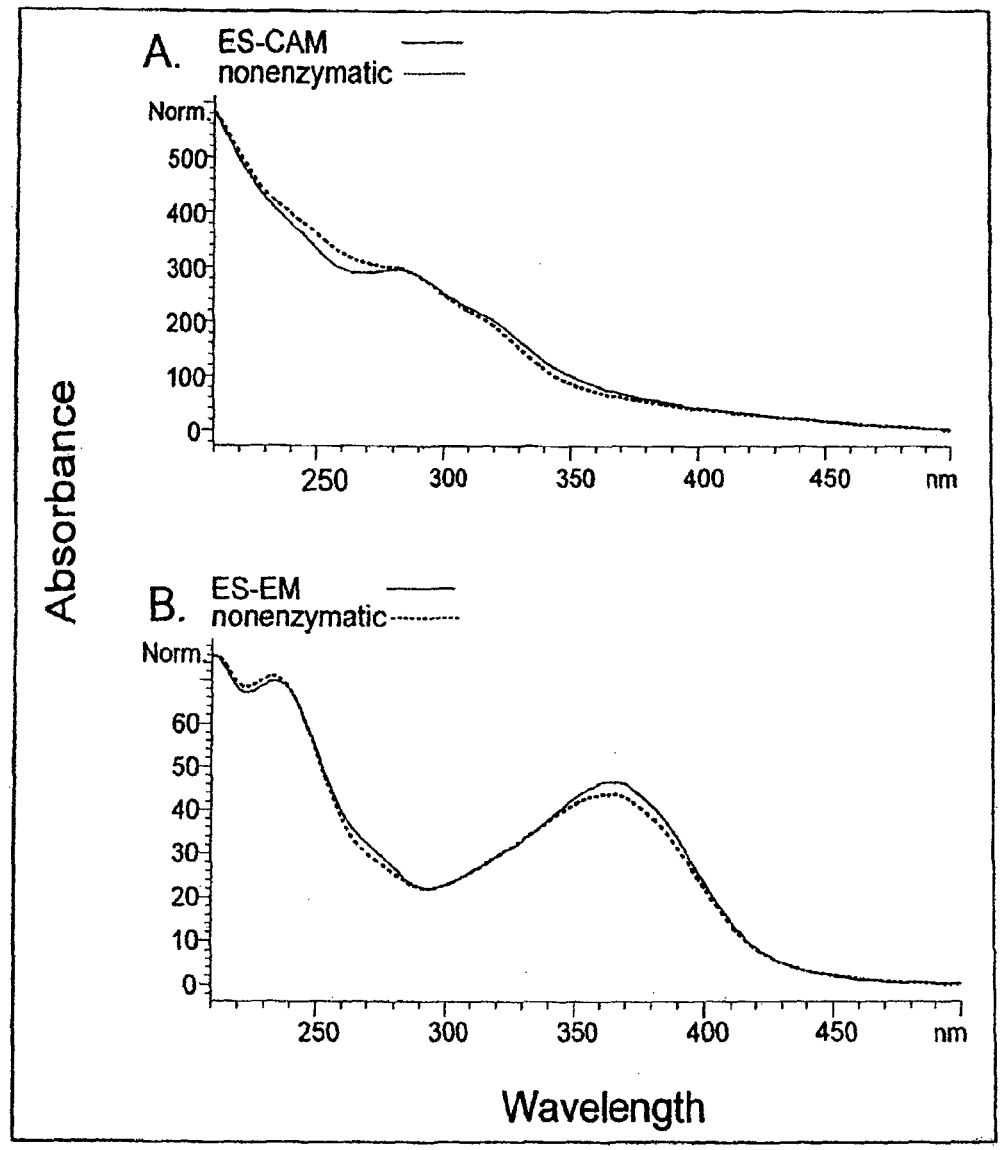
FIG. 3 is the absorbance spectra of ES-CAM and ES-EM and their nonenzymatically synthesized analogues. The UV spectra at the retention times corresponding to the peaks labeled in FIGS. 1 and 2 were recorded with a diode array detector.
Figure 4:
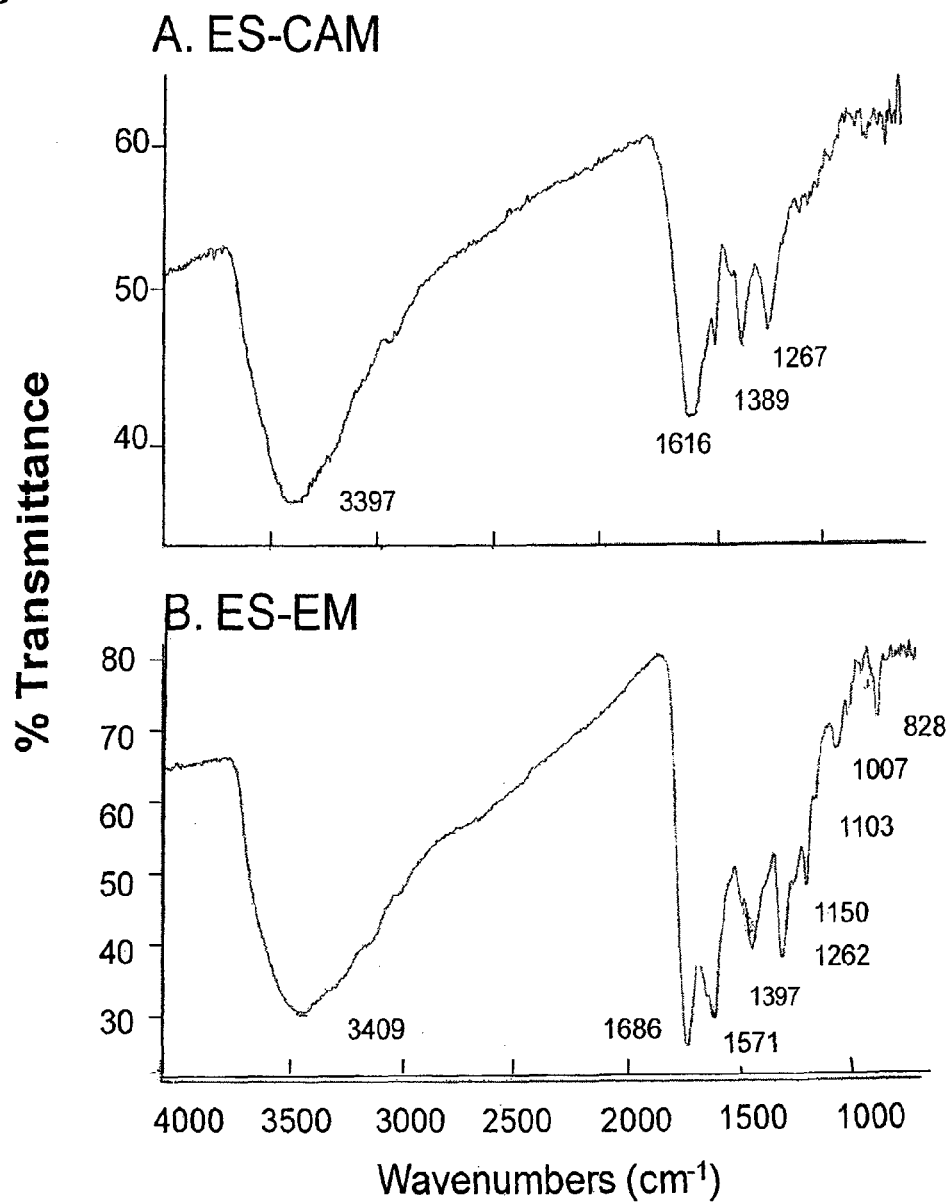
FIG. 4 is the FTIR spectra of ES-CAM and ES-EM. ES-CAM or ES-EM were lyophilized and ground into a powder. A sample of the dry solid was pressed on to the surface of polished potassium bromide salt plate and analyzed using a Thermo-Nicolet Nexus FTIR bench and a Continuum microscope with an MCT detector. The spectra were collected at 8 $cm^{-1}$ resolution.

ES-CAM and ES-EM prepared by the process described above were polymers that are soluble in water and in aqueous buffer solutions with pH's of 4.5 and above. For comparison purposes, nonenzymatically (chemically) synthesized melanins were prepared by oxidizing aqueous solutions of caffeic acid or esculetin at 40° C. and pH 9.0 for a 144 hours period during which humidified room air was continuously bubbled through the reaction mixtures. The final products were isolated by acid precipitation, dialysis, and lyophilization as described above. HPLC-GPC chromatography of ES-CAM at pH 8.6 (FIG. 1A) showed that the product eluted as a single peak with a number average molecular weight of 19.7 kDa. The ultraviolet spectrum of the peak (FIG. 3A) showed a nearly linear increase in absorbance as the wavelength decreased from 300 to 200 nm, a characteristic spectral feature of natural and enzymatically synthesized melanins. Superimposed on this feature were broad, subtle absorbance maxima at 230, 285, and 320 nm, the last two of which are characteristic of cinnamic acid moieties. Under the same conditions, nonenzymatically synthesized melanin prepared from caffeic acid eluted with a molecular weight of 14.7 kDa (FIG. 1B). The UV spectrum of this chemically synthesized melanin was similar to that of its enzyme-synthesized counterpart (FIG. 3A).

Figure 2:
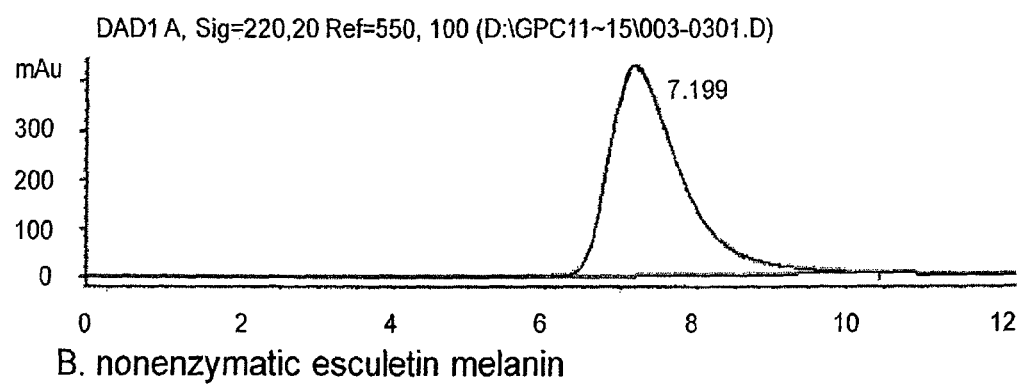
FIG. 2 is a HPLC-GPC chromatogram of enzymatically synthesized esculetin melanin ("ES-EM") and nonenzymatically-synthesized esculetin melanin ES-EM prepared by the process described in this disclosure (A) and nonenzymatically synthesized esculetin melanin (B) were analyzed as described in the legend to FIG. 1.
Figure 2:
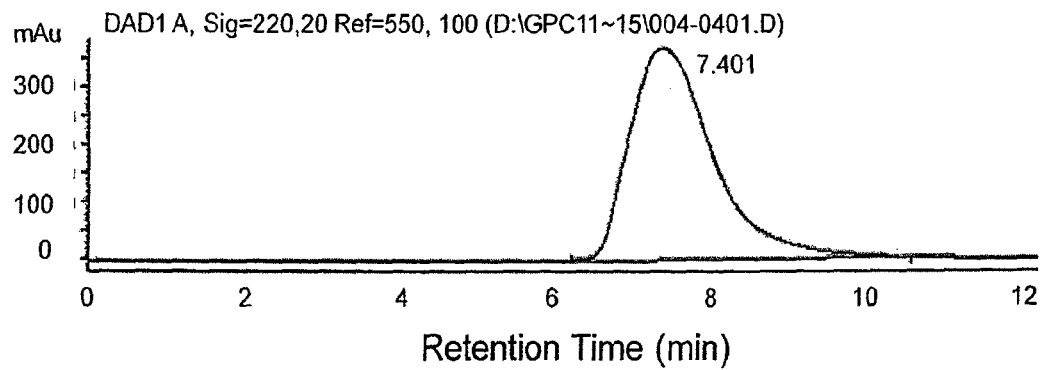

The enzymatically synthesized melanin ES-EM eluted from the HPLC-GPC column with a number average molecular weight of 15.4 kDa (FIG. 2A). The UV spectrum of this product showed major absorbance peaks at 235 and 360 nm and a subtle peak at 270 nm (FIG. 3B). Again, these spectral features were superimposed on the characteristic monotonic absorbance change in the 300 to 200 nm range as described above. Under the same analytical conditions, nonenzymatically synthesized esculetin melanin had a similar UV spectrum (FIG. 3B) but eluted with a molecular weight of 12.9 kDa (FIG. 2B). Note that for both the caffeic acid and esculetin substrates, the melanins production by enzymatic synthesis had higher molecular weights than their nonenzymatically-synthesized counterparts.

FTIR spectroscopy of ES-CAM and ES-EM, which was performed by McCrone Associates, Inc. (Westmont, Ill.), showed that the enzymatically synthesized melanins ES-CAM and ES-EM demonstrated strong absorption bands in 5 regions of the infrared spectrum: in the 3390 to 3450 cm$^{-1}$ region; in the 1600 to 1700 cm$^{-1}$ region; in the 1500 to 1600 cm$^{-1}$ region; in the 1360 to 1410 cm$^{-1}$ region; and in the 1220 to 1280 cm$^{-1}$ region. The broad band at approximately 3400 cm$^{-1}$ is attributed to OH stretching of phenolic and carboxylic acid groups. The bands in the 1500 to 1700 region are attributed to aromatic C═C bonds and aromatic C═C bonds conjugated with C═O and or COO— groups. The bands in the 1300 to 1400 region are attributed to CH2 groups of aliphatic radicals, CH neighboring to OH and COOH groups, and C═O groups of quinones. The bands in the 1200 to 1300 region are attributed to phenolic C—OH stretching. The absorbance bands for ES-CAM were observed at wavenumbers of 3397, 1616, 1508, 1389, and 1267 cm$^{-1}$. The absorbance bands for ES-EM were present at wavenumbers of 3409, 1686, 1571, 1397, and 1262 cm$^{-1}$. The FTIR spectra are similar to those previously reported for certain natural melanins (Savia, V. M. et al., Food Chemistry 2001, 73:177-184; Turick, C. E. Applied and Environmental Microbiology 2002, 68: 2436-2444; Pigment Cell Research 2005, 18: 130-135; and Liu, Y. et al., Photochemistry and Photobiology 2005, 11:135-144) and for melanins chemically synthesized from catecholamines or quinones (Cataldo, F. Polymer International 1998, 46:263-269).

Figure 5:
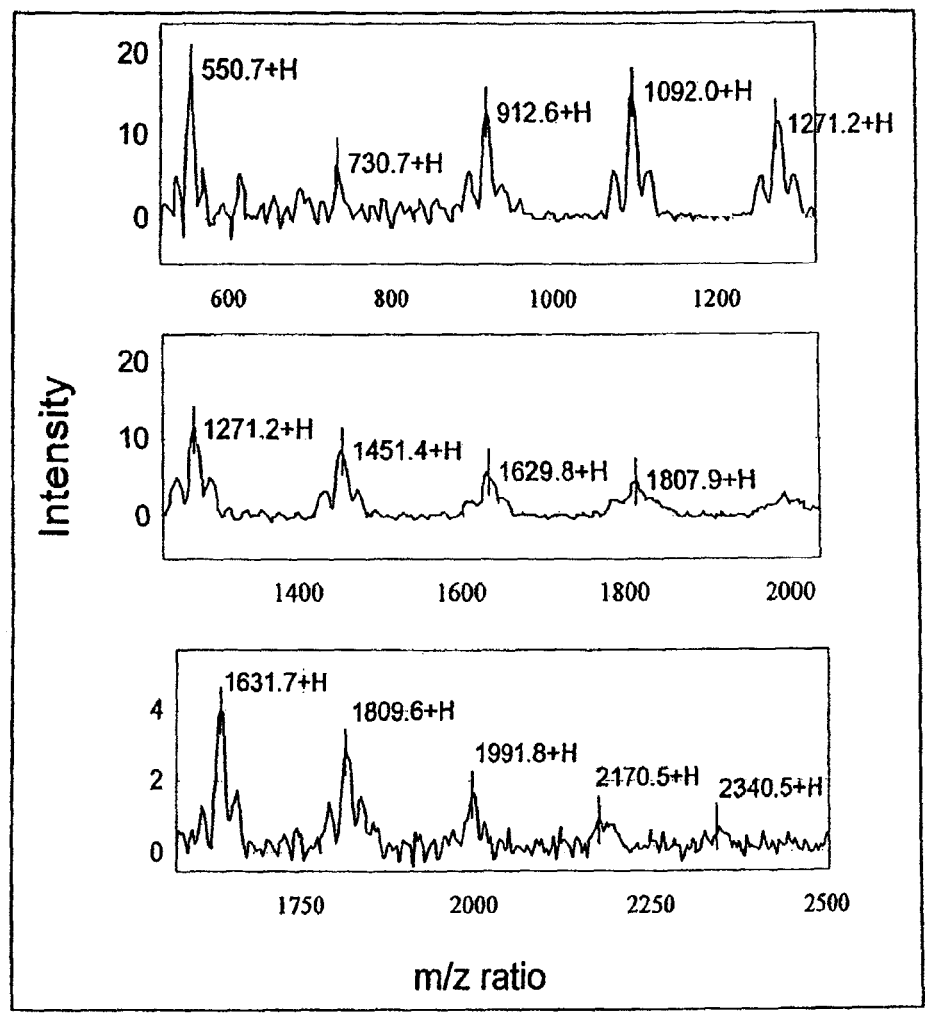
FIG. 5 is a MALDI-TOF mass spectrum of ES-EM. ES-EM was diluted with a matrix consisting of 10 mg/mL, DHBA in ethanol/water ITF A, 50/50/0.1 (v/v/v), spotted on a gold target, and analyzed with a Ciphergen PBS II mass spectrometer. The spectrometer was operated in the positive ion mode at a laser intensity of 240 and a sensitivity of 6.

ES-CAM and ES-EM synthesized by our enzymatic processes were analyzed by MALDI-TOF mass spectrometry by M-Scan Inc. (West Chester, Pa.). High resolution analysis in the positive ion mode using a matrix of Dithranol+AgTFA showed that both ES-CAM and ES-EM had spectra characteristic of polymers with number average molecular weights of approximately 3.6 kDa and 3.3 kDa, respectively. Both enzymatically synthesized melanins had mass spectra that indicated high degrees of polydispersity. Both melanin products contained multiple molecular species (i.e, oligomers) that differed by 24 m/z units. This mass difference is consistent with the presence of oligomers containing multiple intrachain ring closures and extended polynuclear (graphite-like) structures (Brown, C. E. and Cody, R. B. J. Polymer Sci. Part C: 24,519-528(1986)). Further analysis of ES-EM under different analytical conditions using a more acidic DHB matrix gave a spectrum characterized by multiple clusters of peaks (FIG. 5). The major components of each cluster had m/z ratios of 550.7, 730.7, 912.6, 1092.0, 1271.2, 1451.4, 1629.8, 1807.8, 1991.8, 2170.5, and 2340.5. The incremental difference of 179 amu between the major peaks of each cluster is close to the molecular mass of esculetin (178.15 g/mol), suggesting that ES-EM contains esculetin polymers with different degrees of polymerization. These results also suggest that in aqueous solution, ES-CAM and ES-EM exist as aggregates of low molecular weight oligomers.

Process for Chemical Production of Melanins.

18 melanins were prepared from commercially available precursors, obtained from Sigma-Aldrich (St. Louis, Mo.). The melanins are designated as C1 to C18, listed in table 4.

15 mg of the precursor was dissolved in 7 mL of 0.2 M sodium carbonate buffer, pH 10.6 in a glass test tube. Then 30 µL of a 5 mg/mL solution of salcomine (N,N'-bis(salicylidine)ethylene diiminocobalt (II) (Sigma Aldrich, catalog No. 274712) in dimethylformamide was added into the solution. The tube was placed in a block heater at 45° C. The outlet of a capillary tubing was inserted at the very bottom of the test tube, the tube was capped, and a continuous stream of humidified room air (flow rate 25 mL/min) was bubbled through the reaction mixture. At 12 hour intervals, sufficient deionized water was added to the reaction mixture to restore its total volume to 7 mL. After 48 hour, the pigmented reaction mixture was cooled to ambient temperature, transferred to Spectra/Por 6 dialysis tubing (1000 Da MWCO, Spectrum Laboratories Inc., Rancho Dominguez, Calif.) and dialyzed against 4×4 L changes of deionized water. The dialyzed product was lyophilized in a tared vessel, and recovered as a dry solid. The polymer products were recovered at yields ranging from 11% to 89% (median 59%) as shown in Table 4.

The chemical synthesis process was also scaled up by a factor of 10. The reaction mixtures of 150 mg precursor, 70 mL buffer, 300 µL of 5 mg/mL salcomine were incubated in pear flasks for 48 hours at 45° C. with a bubbling stream of air at a flow rate of 125 ml/min. The percent yields were similar to those reported in Table 4 and the weights of the final products were increased by approximately 10-fold.

Physical Properties of Melanins Prepared by Chemical Synthesis.

Figures 1, 6A:
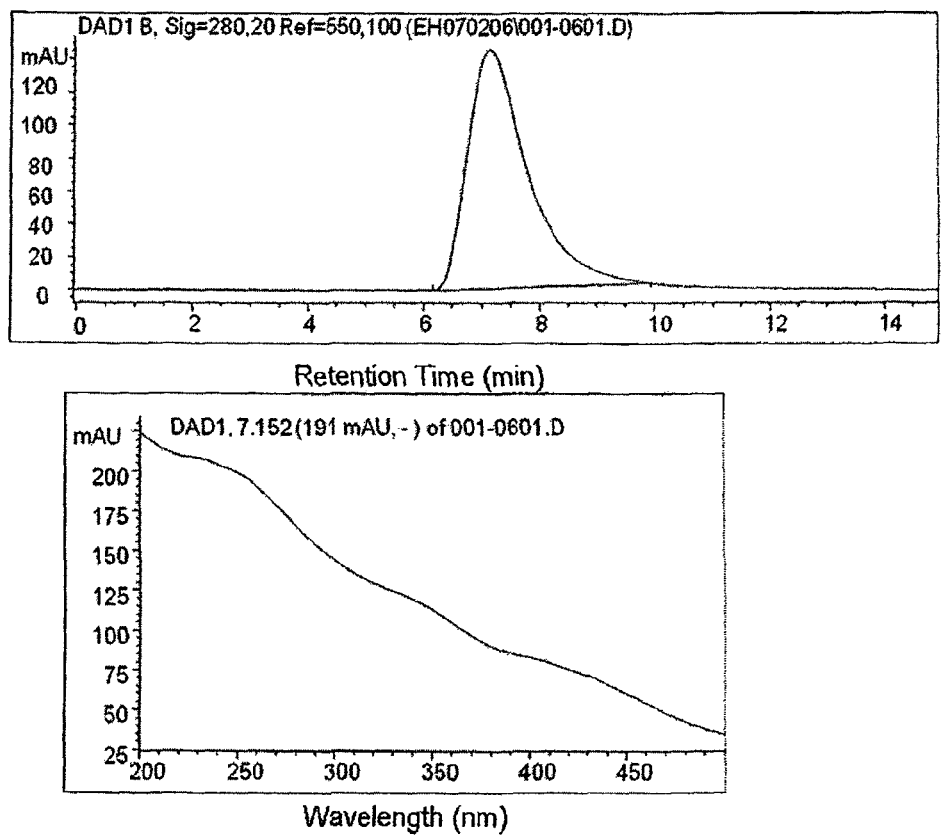
FIG. 6a is the HPLC-GPC chromatograms and UV spectra of chemically synthesized melanins C1-C6. The compounds are listed in table 4.
Figures 2, 6A:
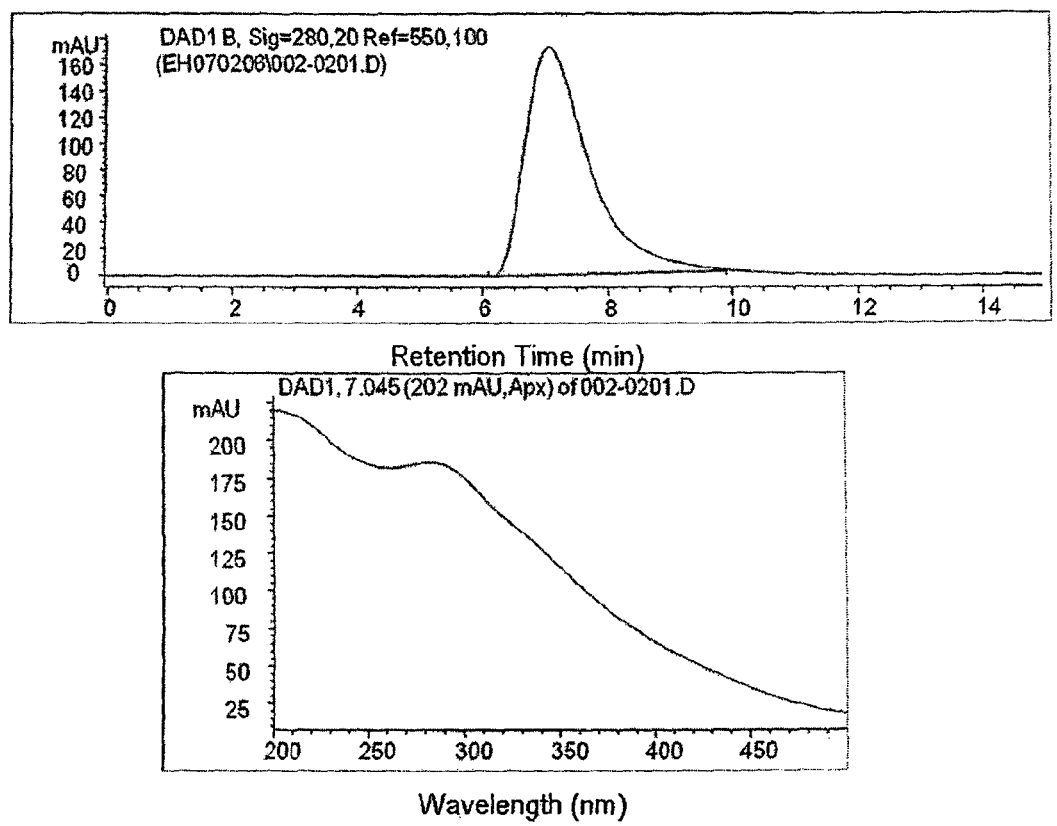
Figures 3, 6A:
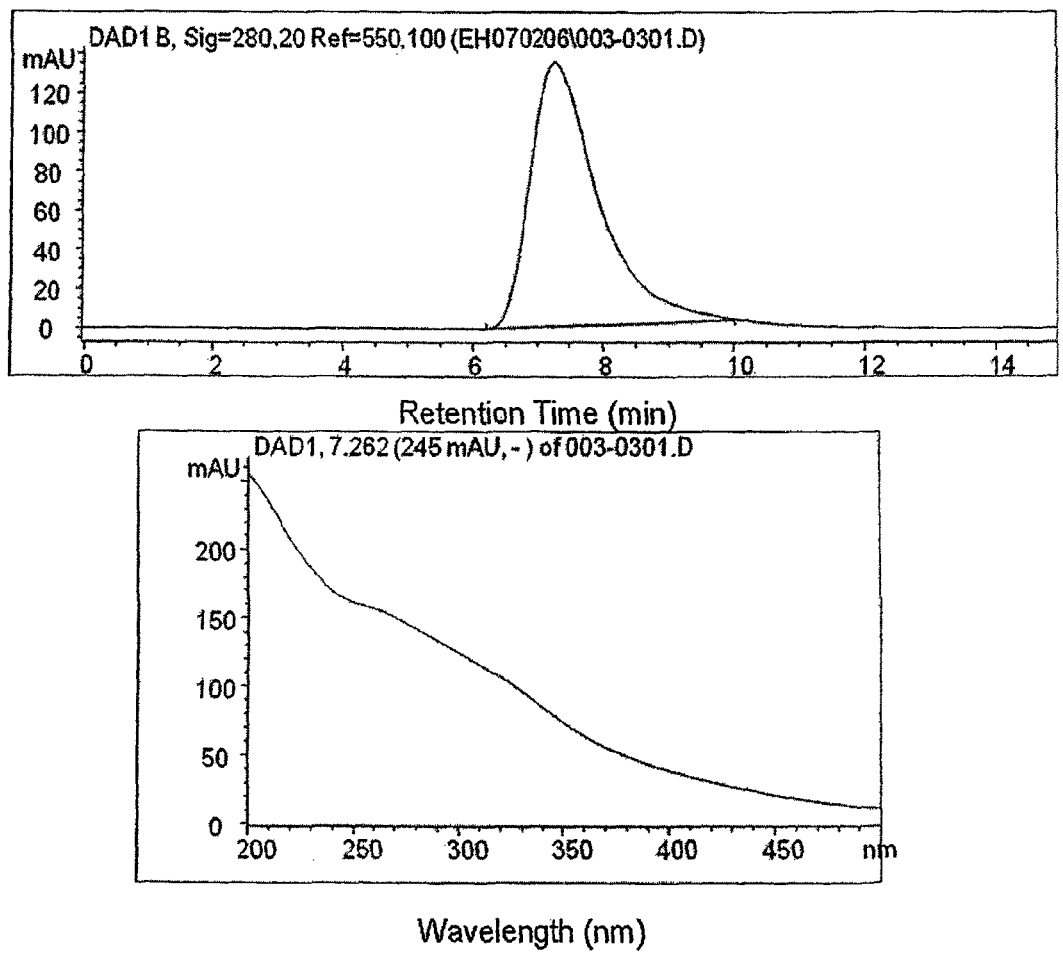
Figures 4, 6A:
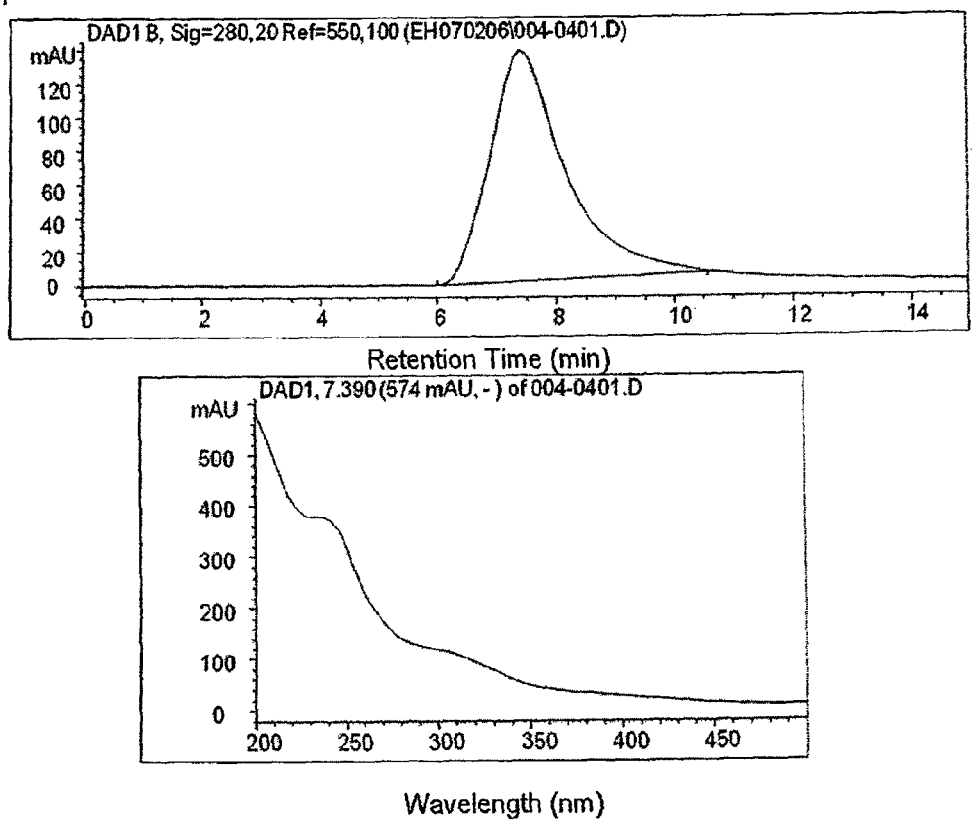
Figures 5, 6A:
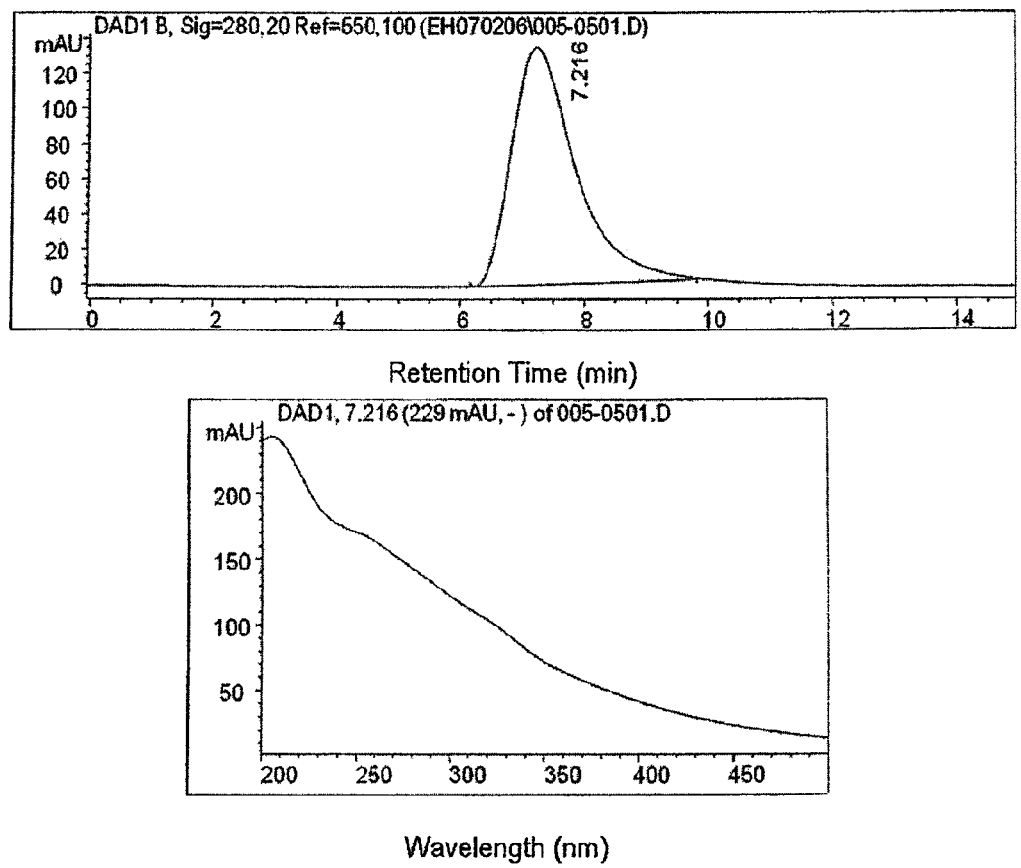
Figures 6, 6A:
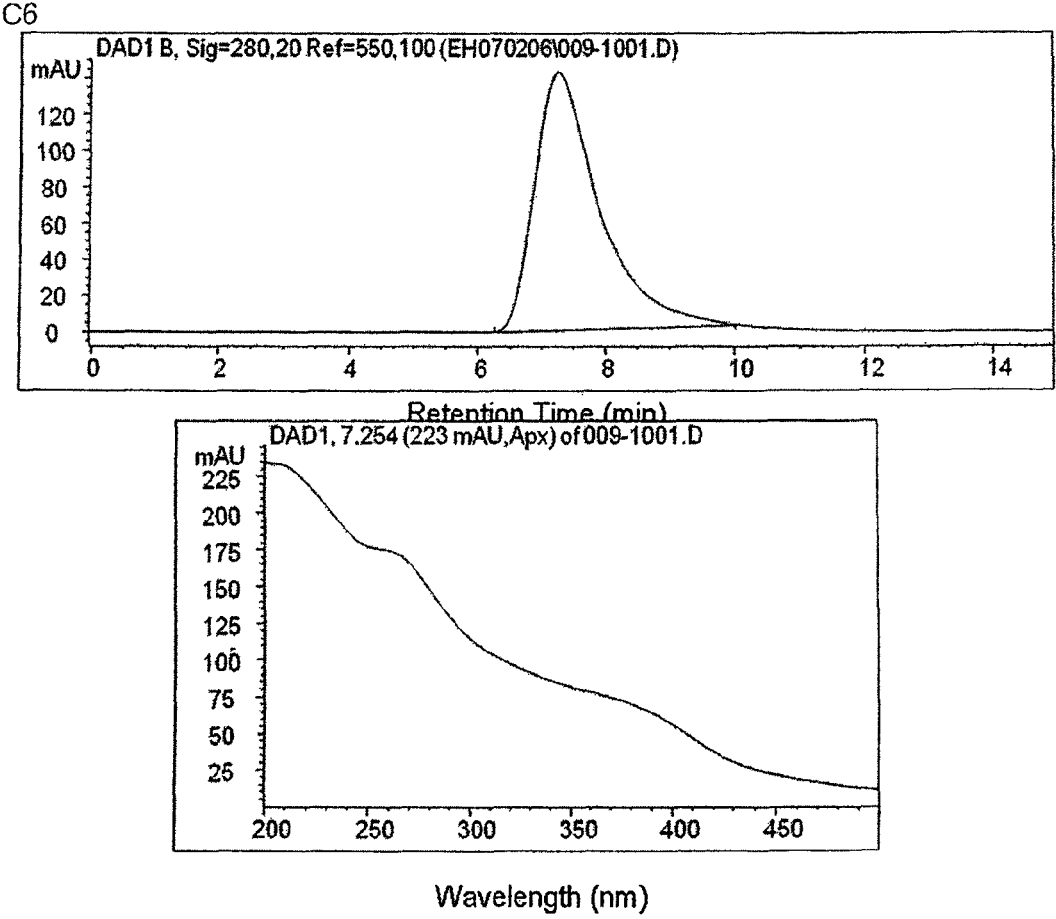
Figures 1, 6B:
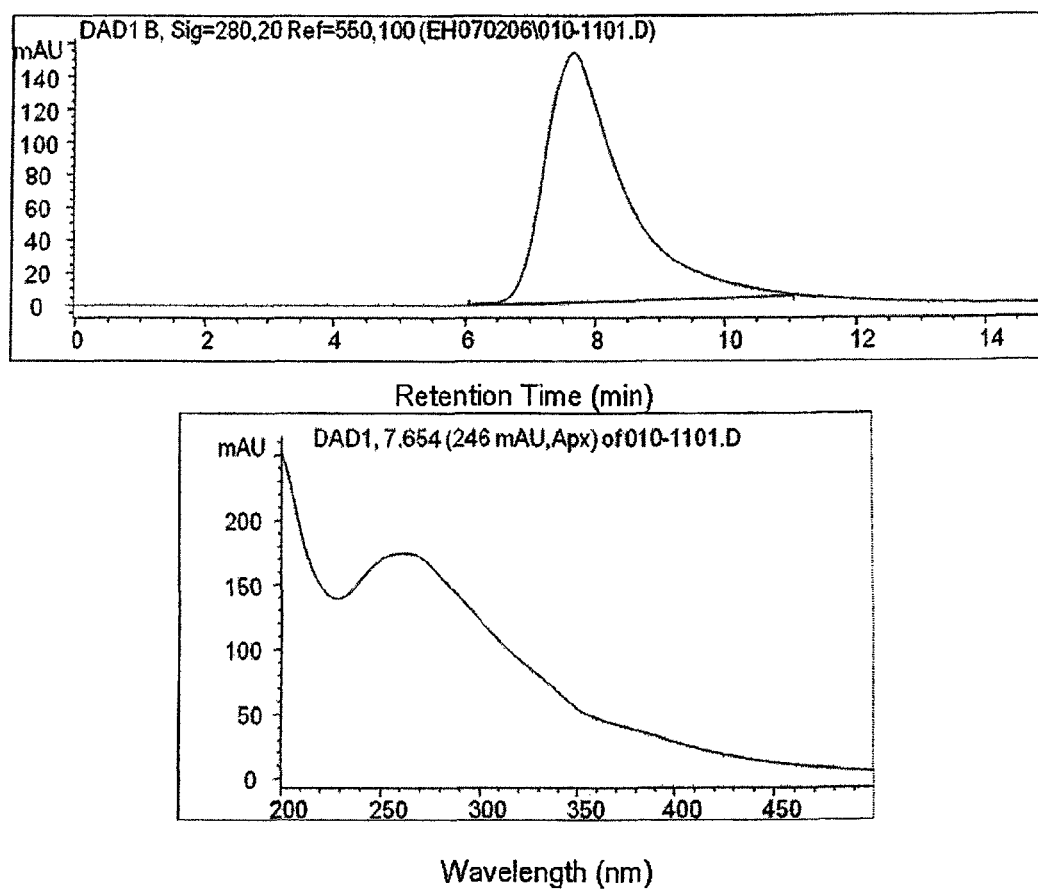
FIG. 6b is the HPLC-GPC chromatograms and UV spectra of chemically synthesized melanins C7-C12. The compounds are listed in table 4.
Figures 2, 6B:
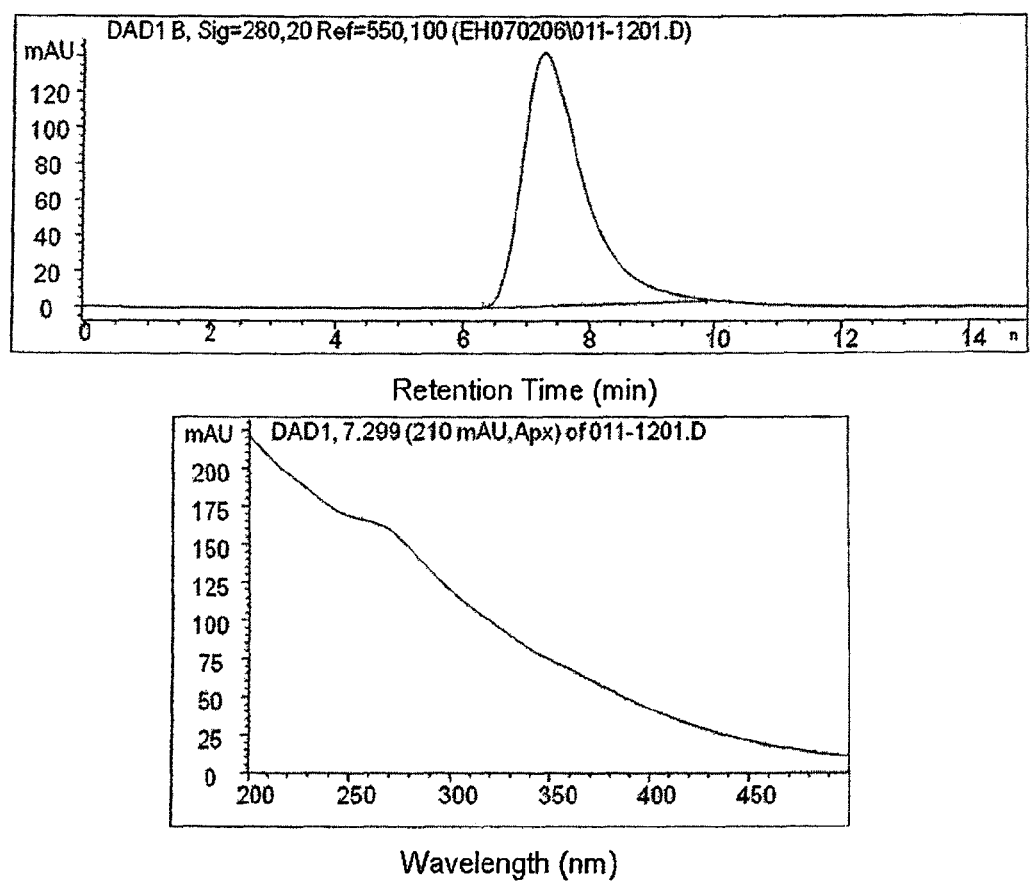
Figures 3, 6B:
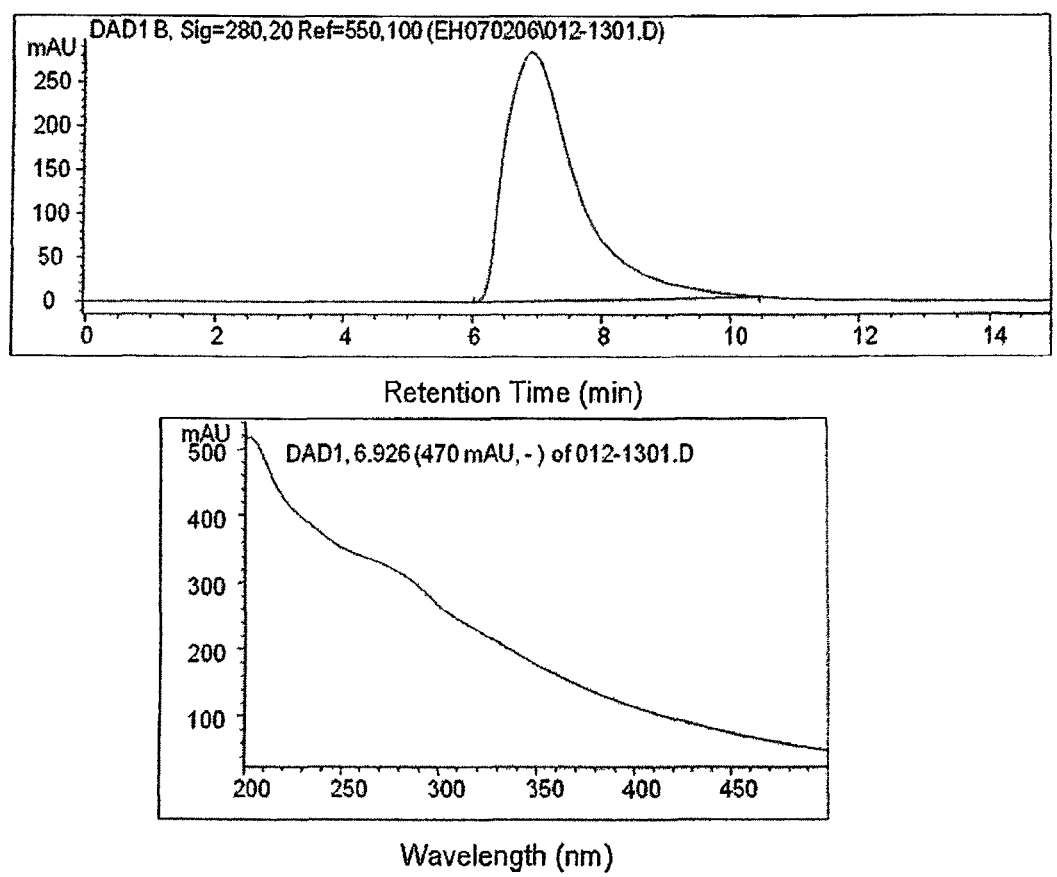
Figures 4, 6B:
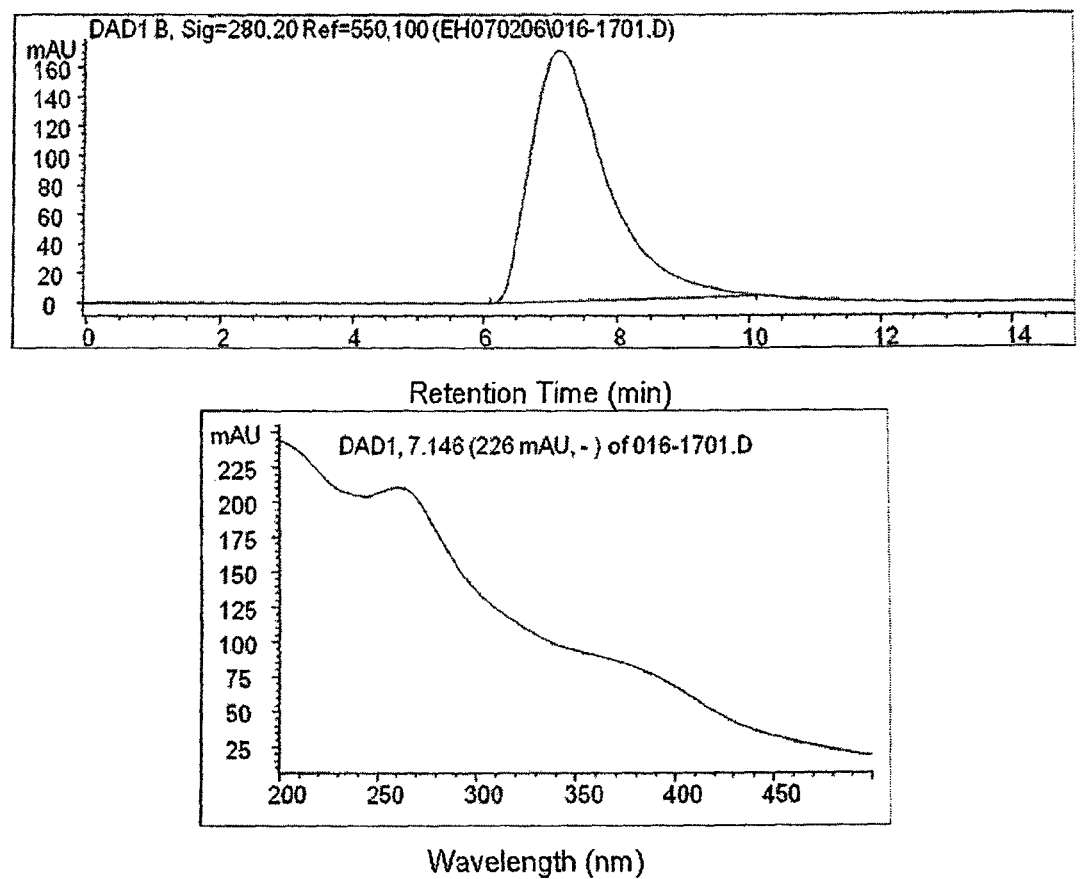
Figures 5, 6B:
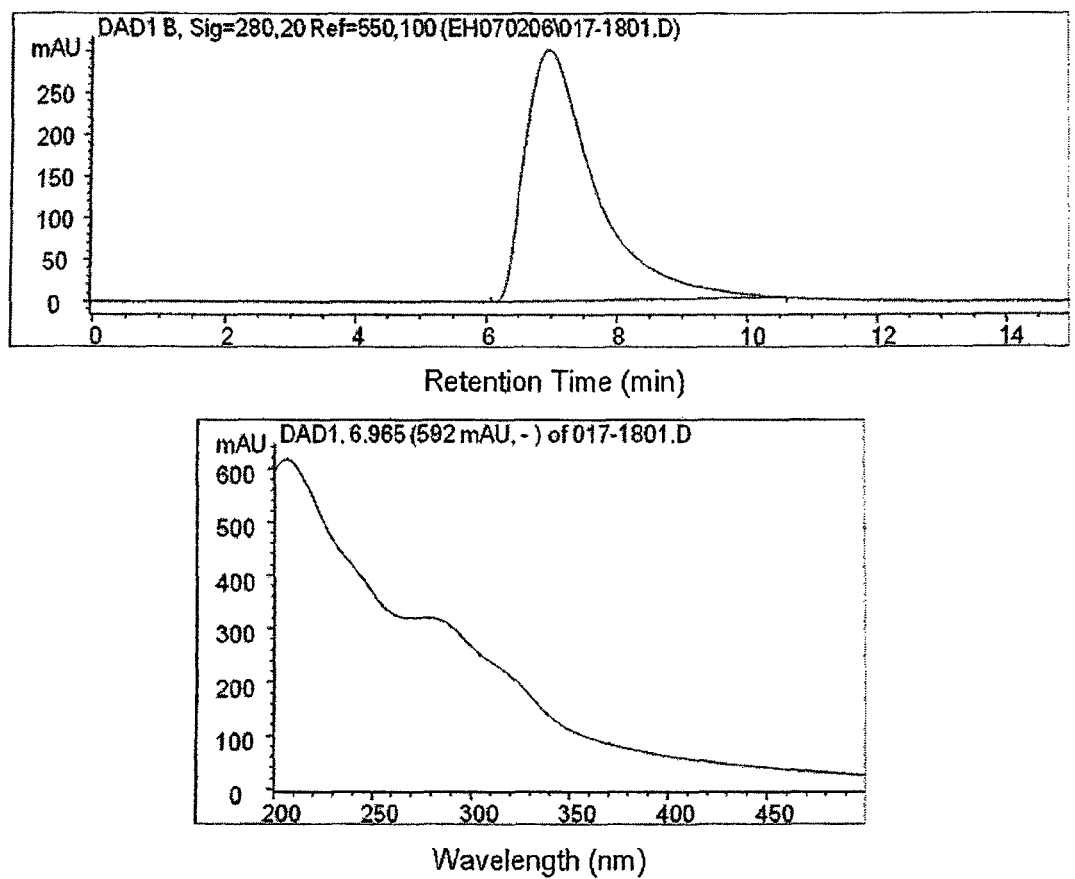
Figures 6, 6B:
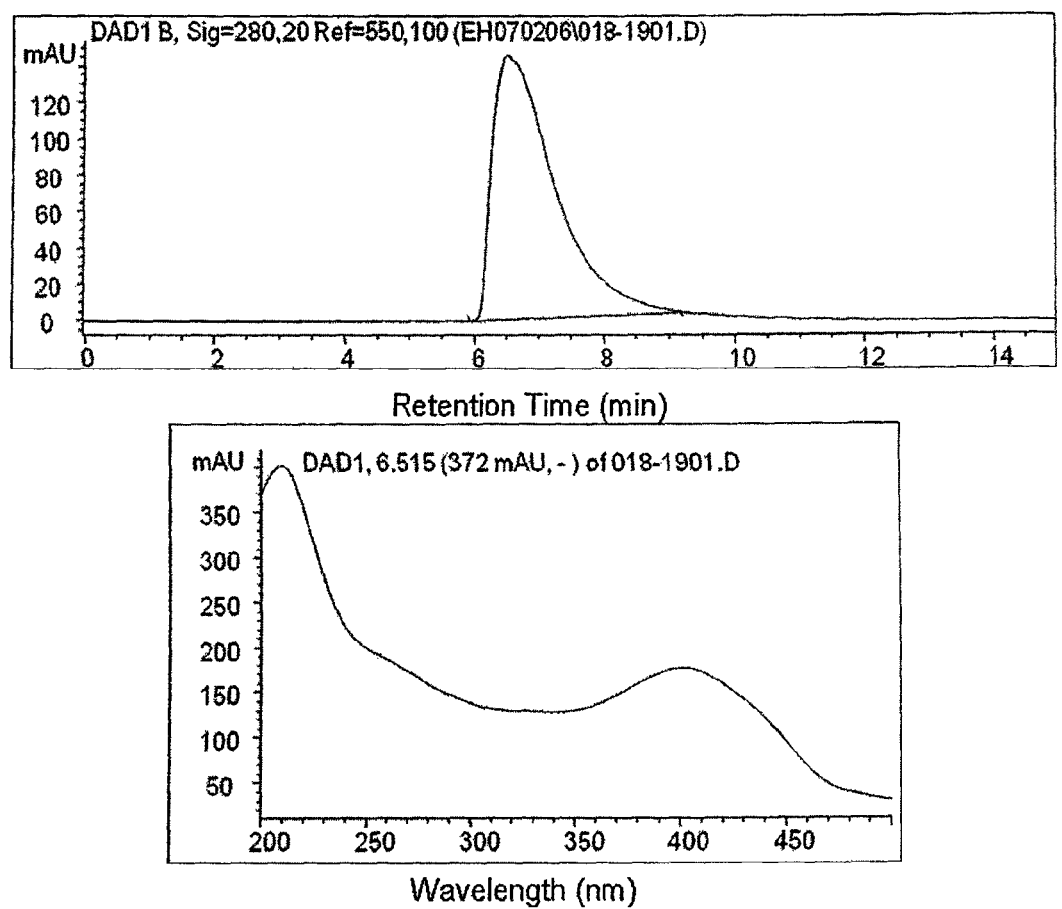
Figures 1, 6C:
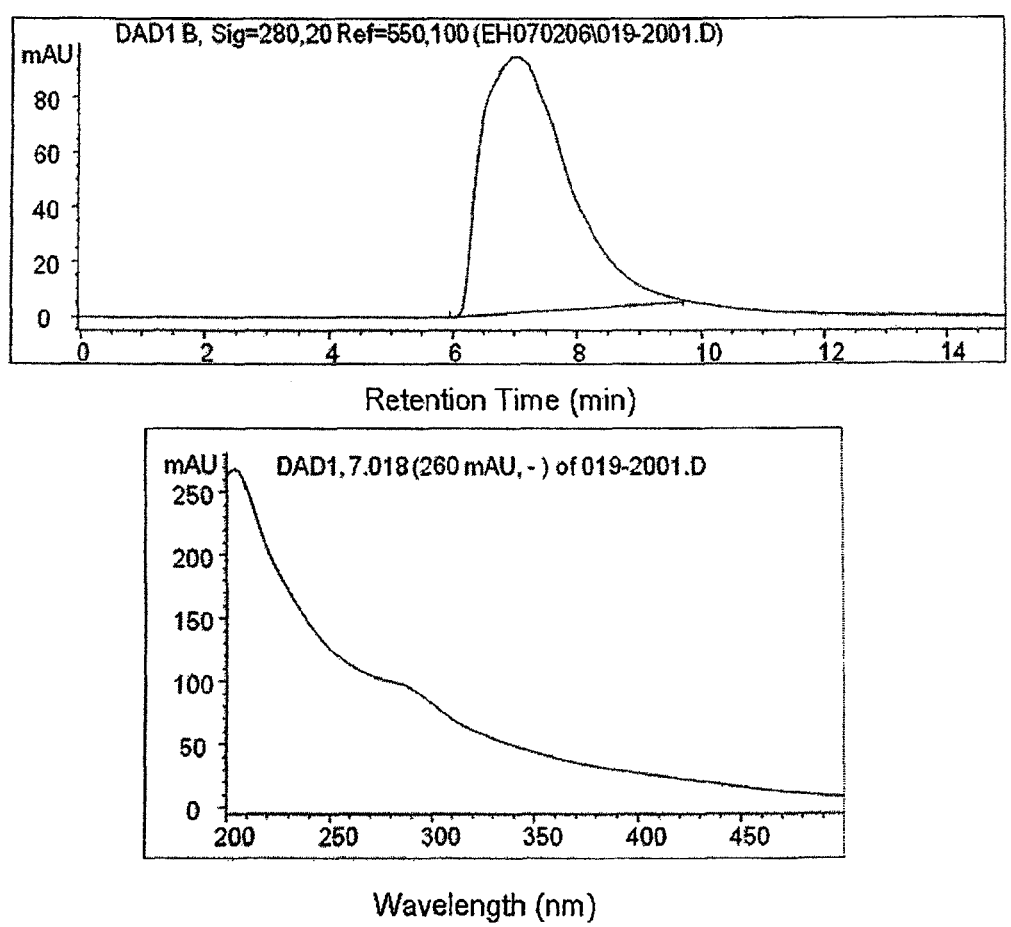
FIG. 6c is the HPLC-GPC chromatograms and UV spectra of chemically synthesized melanins C13-C18. The compounds are listed in table 4.
Figures 2, 6C:
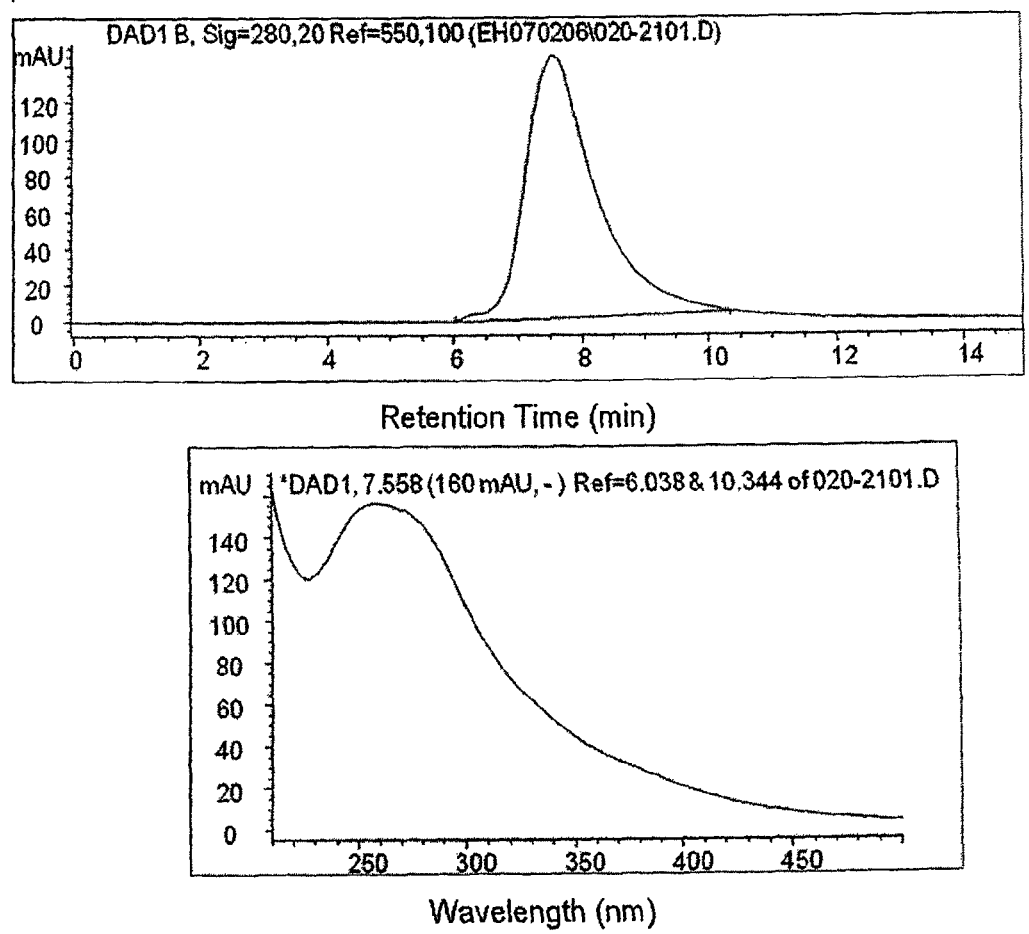
Figures 3, 6C:
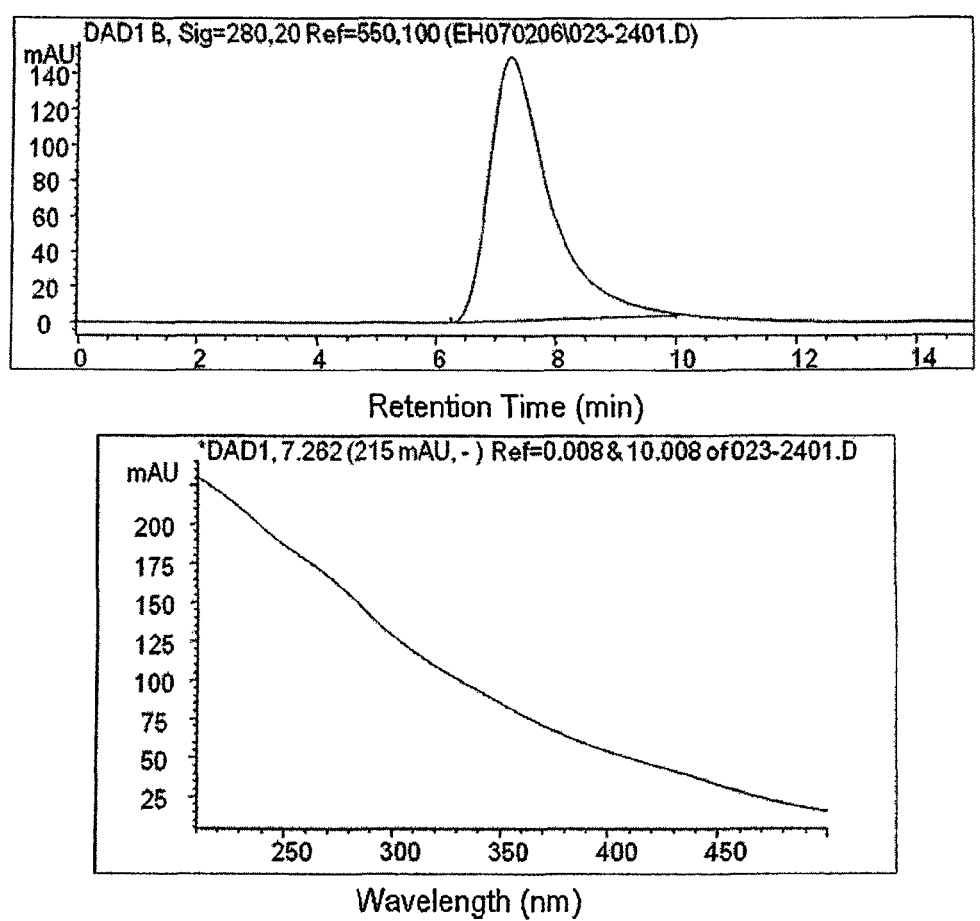
Figures 4, 6C:
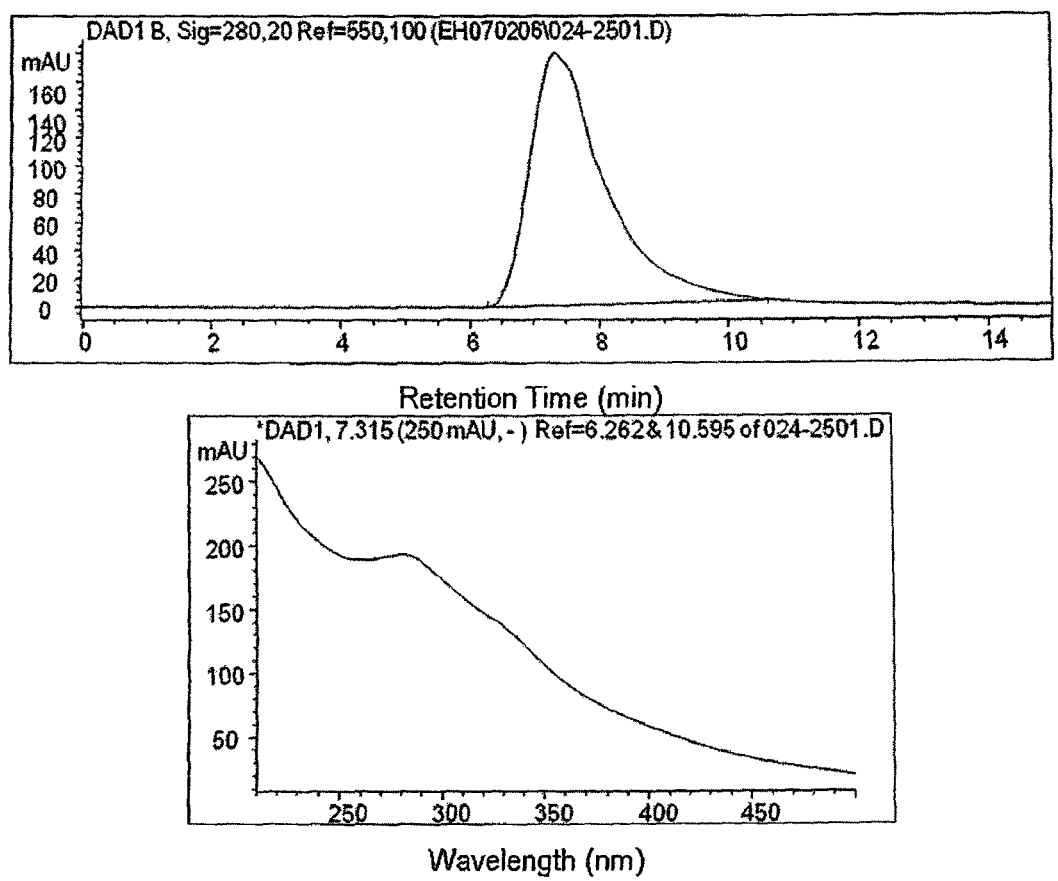
Figures 5, 6C:
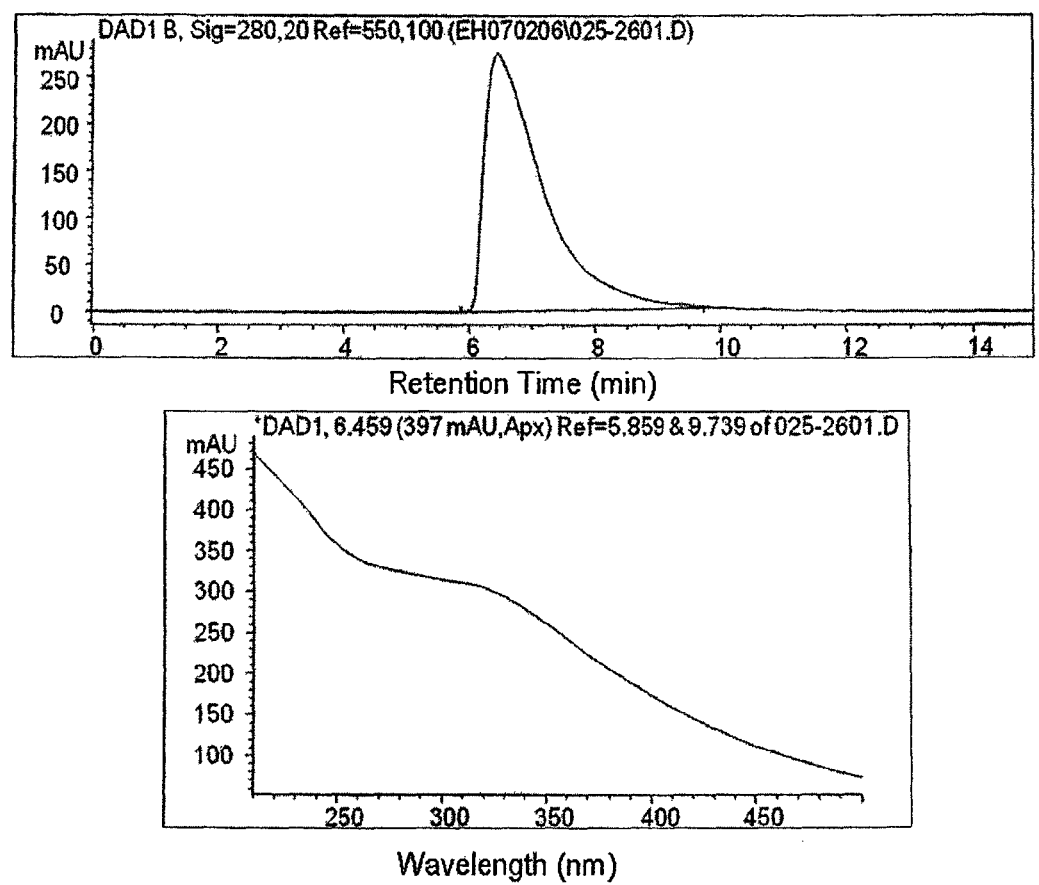
Figures 6, 6C:
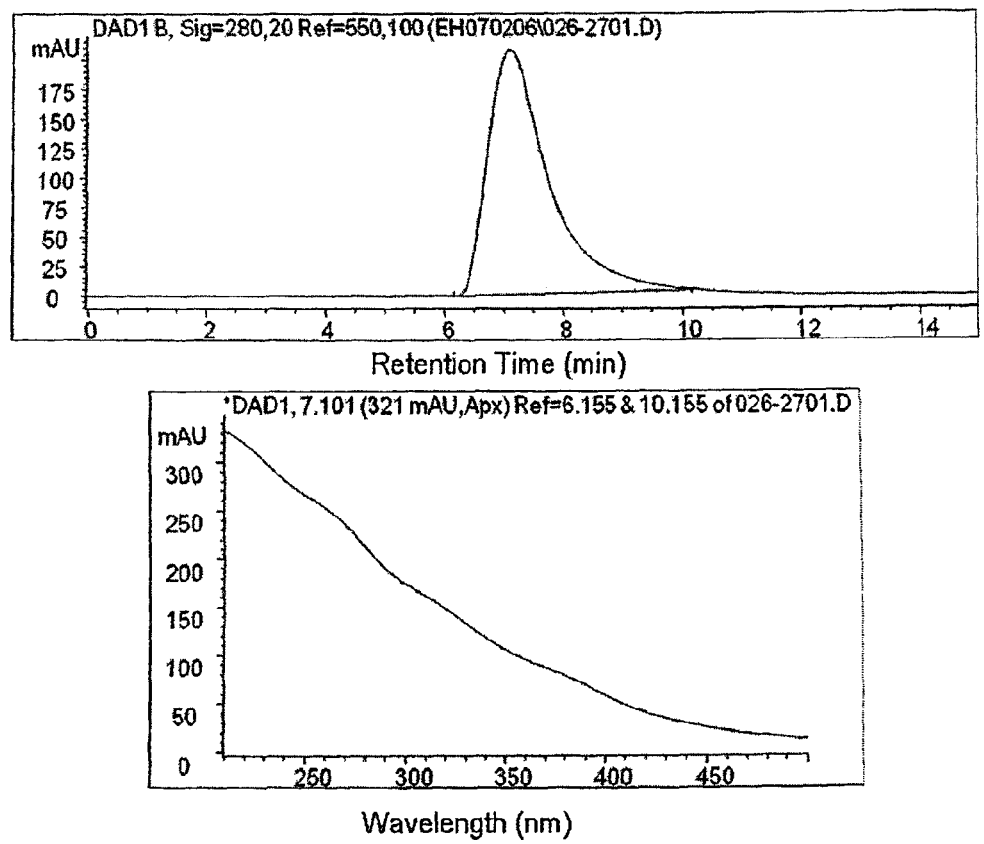
Figures 1, 7A:
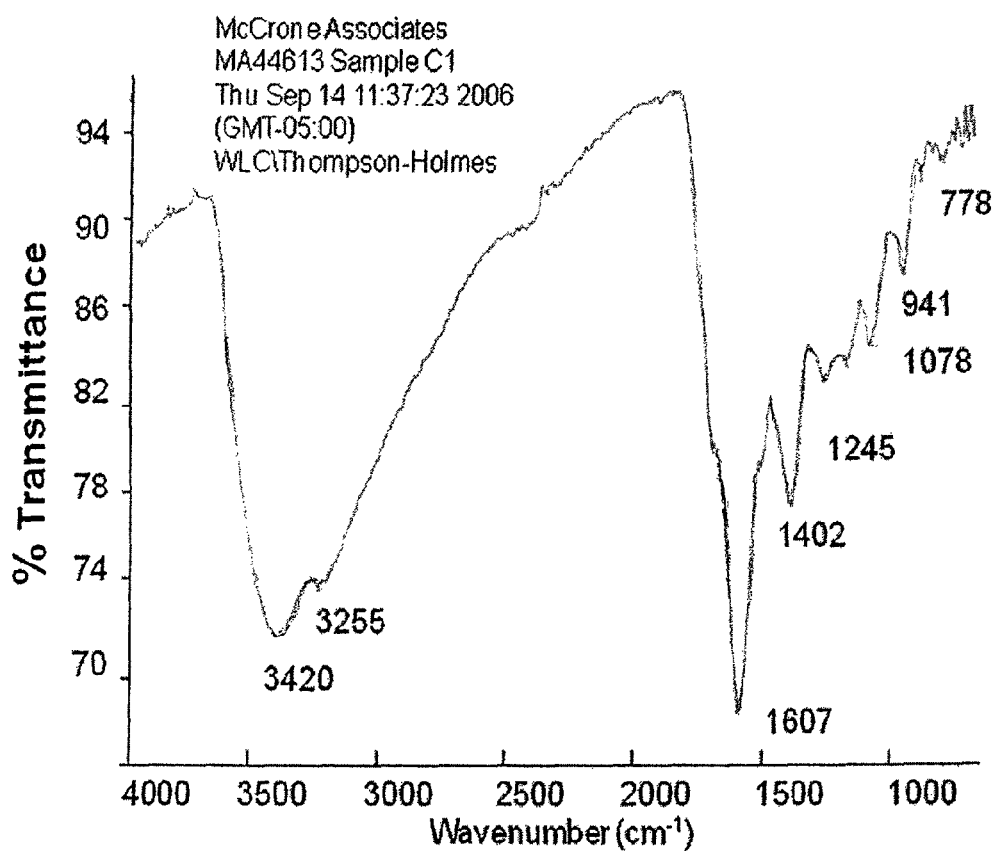
FIGS. 7a is the FTIR spectra of chemically synthesized melanins C1, C2, C4, and C9.
Figures 2, 7A:
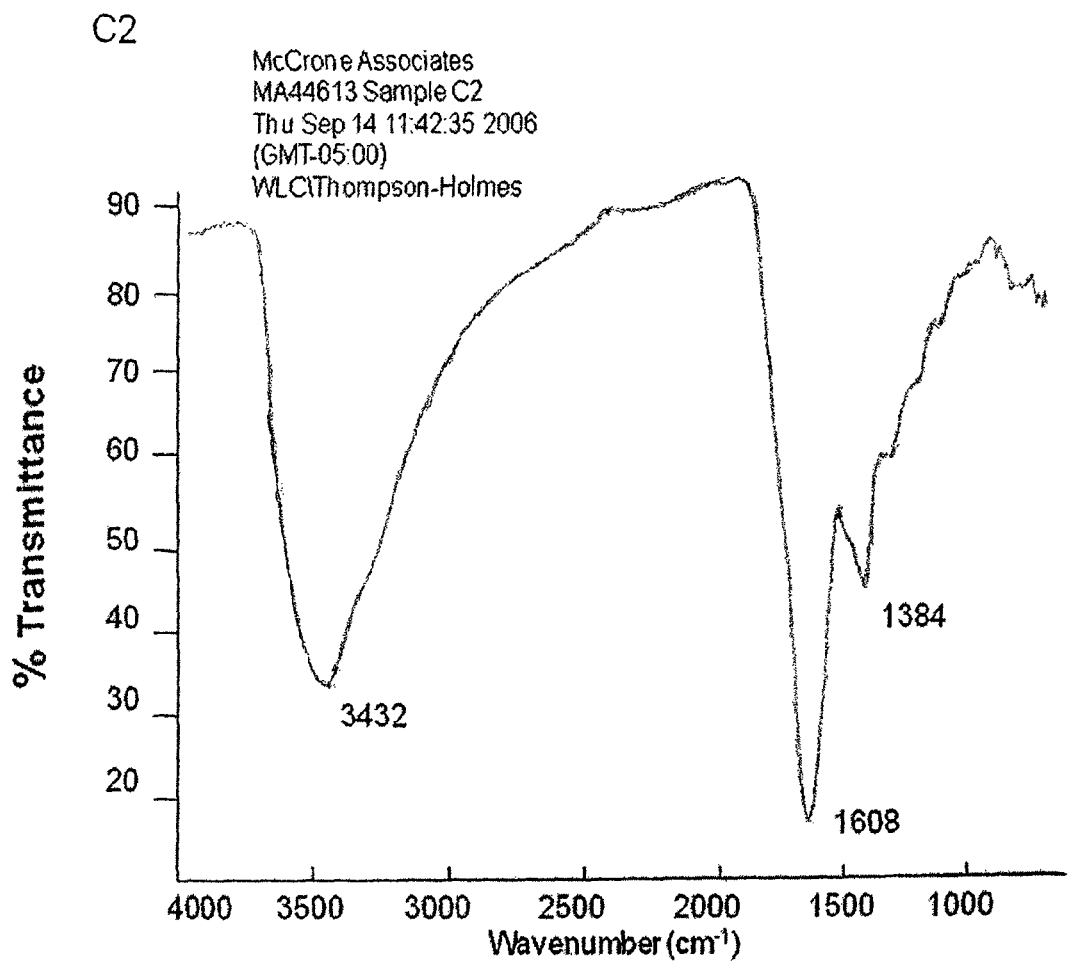
Figures 3, 7A:
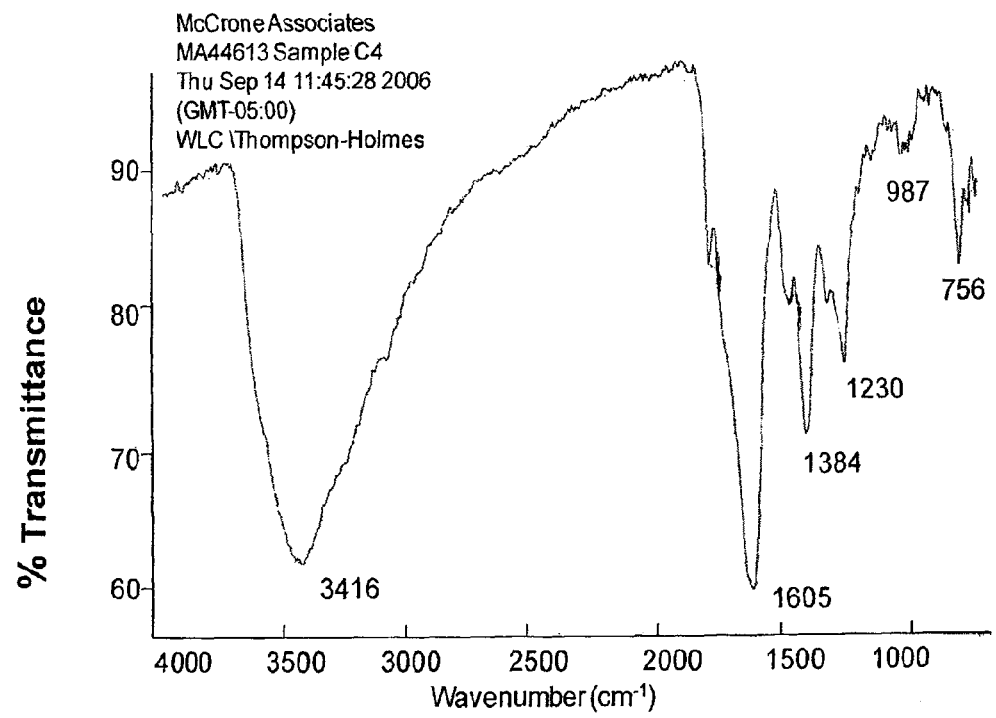
Figures 4, 7A:
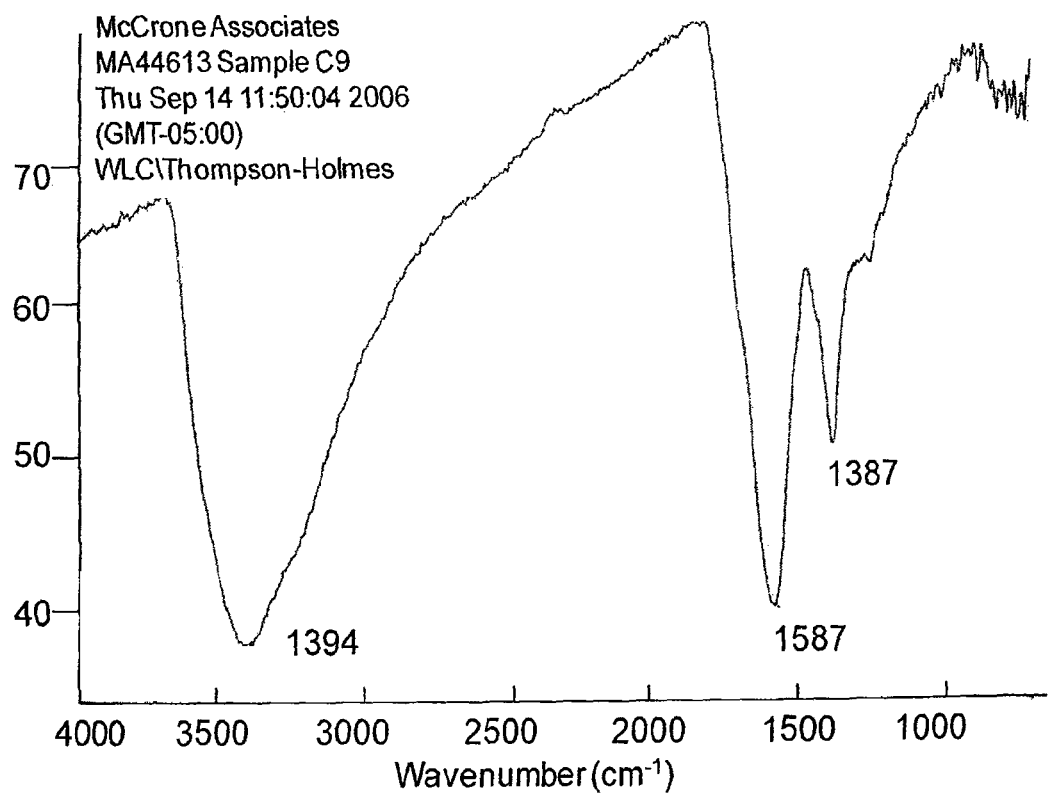
Figures 1, 7B:
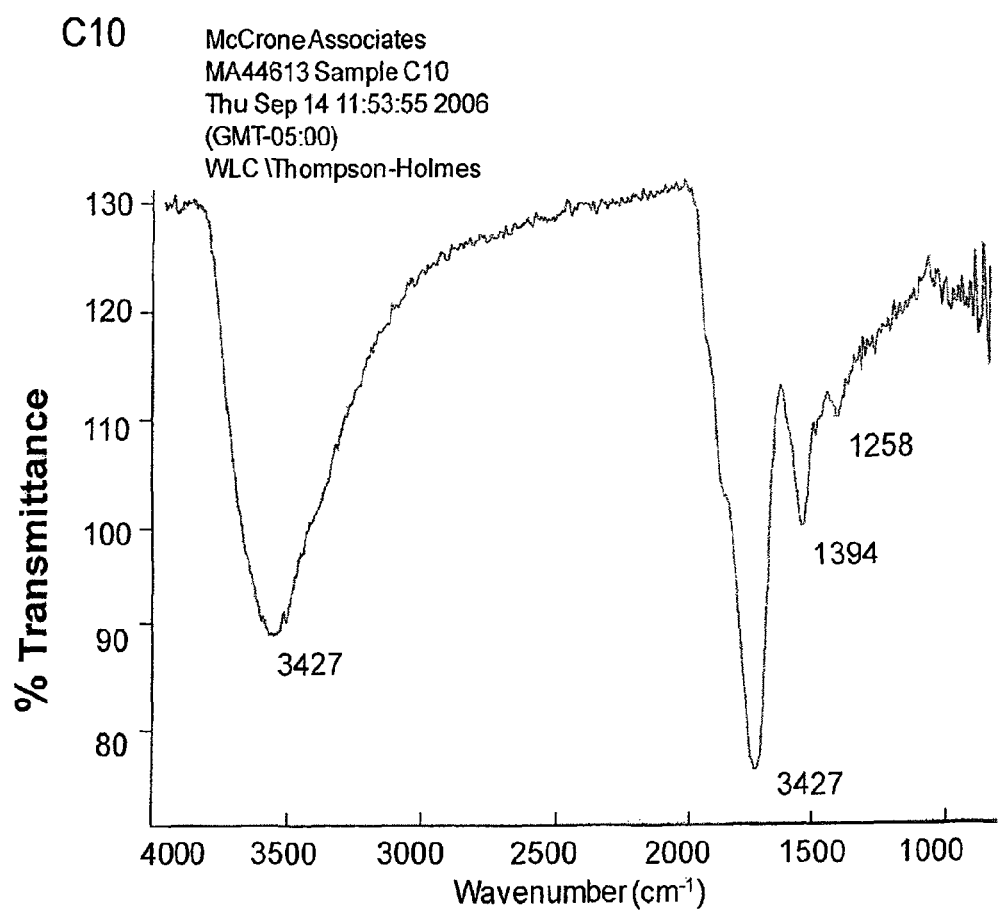
FIGS. 7b are the FTIR spectra of chemically synthesized melanins C10, C11, C12, and C17.
Figures 2, 7B:
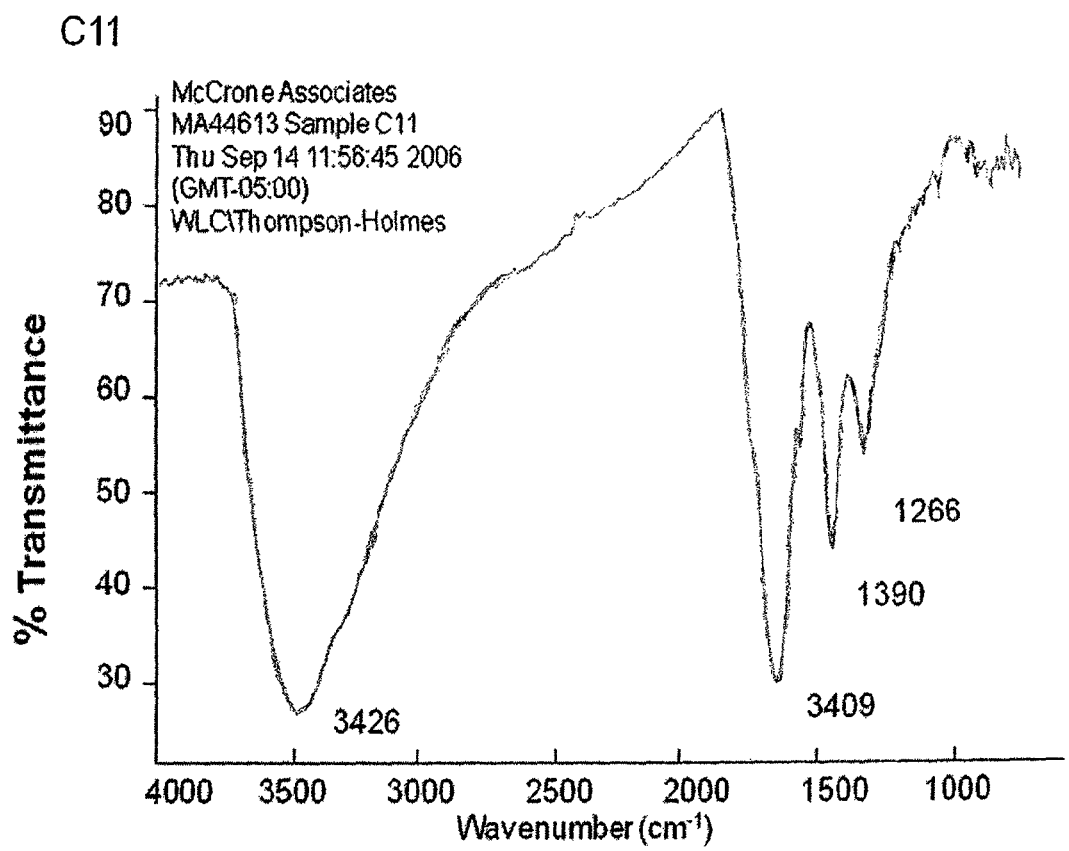
Figures 3, 7B:
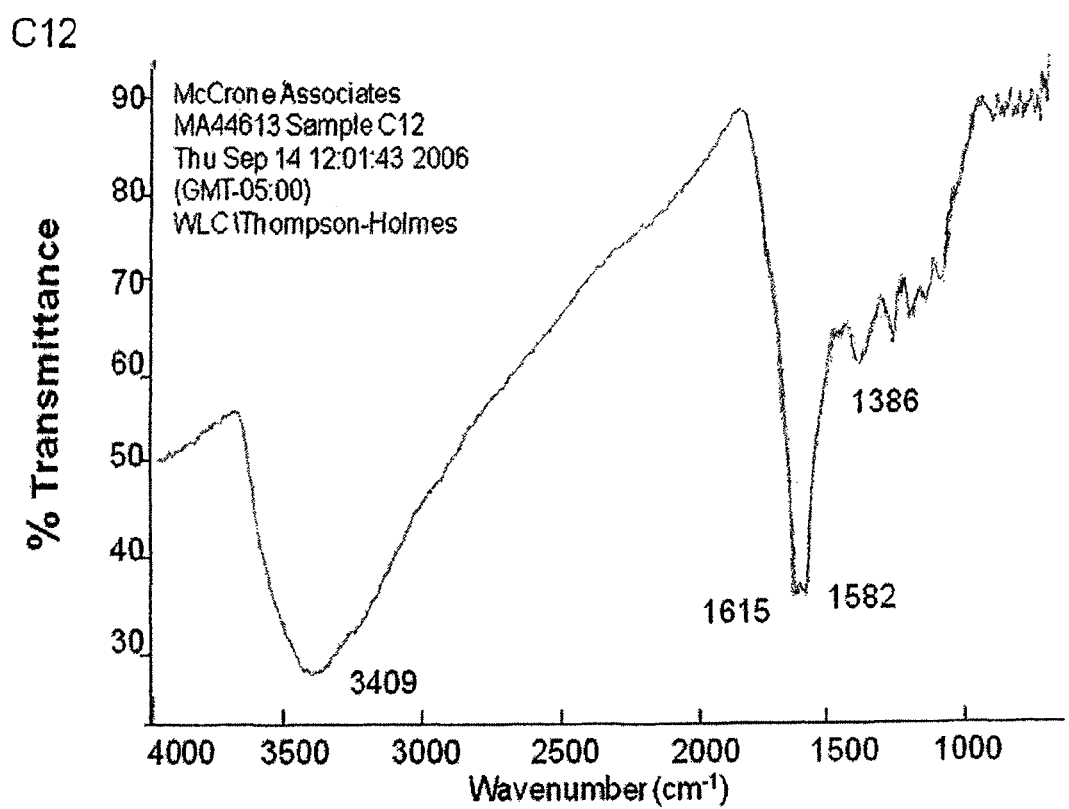
Figures 4, 7B:
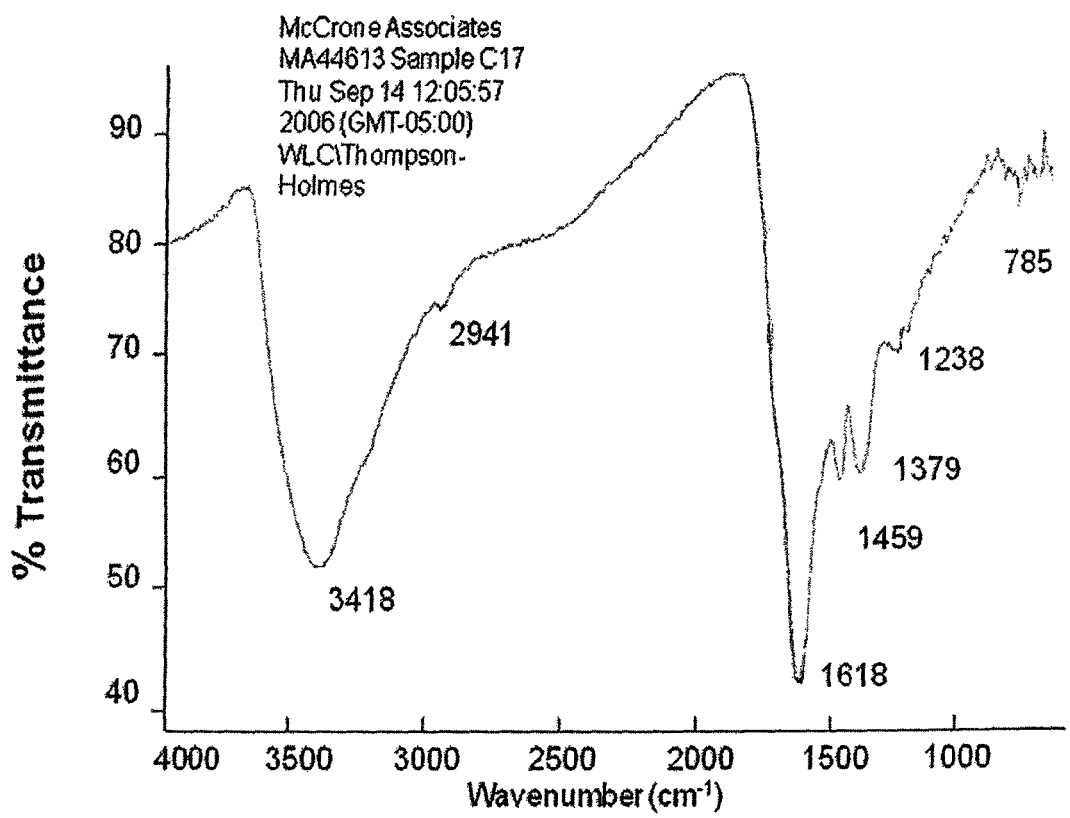

The results of HPLC-GPC chromatography of the chemically synthesized melanin polymers and their ultraviolet spectra are presented in FIGS. 6a, 6b, and 6c. The number average molecular weight of each compound based on its elution volume relative to those of dextran standards of known molecular weights are presented in Table 4. Eight of the chemically synthesized polymers were analyzed by FTIR (FIGS. 7a and 7b). The spectra are similar to those previously obtained for natural and enzymatically synthetic melanins. The differences in the FTIR spectra of ES-CAM and C11 and between the FTIR spectra of ES-EM and C10 illustrate structural differences in polymers made from the same precursors by the two different processes—one enzymatic and one chemical.

Antiviral Activities of the Enzymatically and Chemically Synthesized Melanins.

The antiviral activities of the enzymatically synthesized melanins ES-CAM and ES-EM are summarized in Tables 3 through 14.

TABLE 3

Anti-Viral Potency of ES-CAM and ES-EM (ED50, µg/mL)[1].

| Compound: | ES-CAM | ES-EM |
|---|---|---|
| Precursor: | Caffeic Acid | Esculetin |
| Virus Strain[2] | | |
| HSV-1F | 1.00 | 2.00 |
| Clin 61665 | 1.00 | 2.00 |
| 15985 (AR) | 1.00 | 2.00 |
| Clin 10301(AR) | 1.00 | 1.00 |
| HSV-2G | 0.25 | 1.00 |
| Clin 23235 | 0.50 | 2.00 |
| Clin 27071 | 0.25 | 1.00 |
| Clin 16064 (AR) | 0.50 | 1.00 |
| CMV AD169 | 0.25 | 1.00 |
| Clin D16 (GR) | 0.25 | 0.50 |
| Clin OBR (GR) | 0.12 | 0.50 |
| HIV BAL strain | 0.21 | 0.036 |

[1]The anti-HSV assay was an in situ ELISA performed with minor modifications (Thompson and Dragar, Phytotherapy Research 18: 551-555, 2004). The anti-CMV assay was a plaque reduction assay and was performed with minor modification (Sullivan, V., et.al., Antimicrobial Agents and Chemotherapy 37: 19-25, 1993).
[2]Clin: virus strain is a primary isolate obtained from an infected human; AR: acyclovir resistant; GR: ganciclovir resistant.

The results in Table 3 show that both compounds have high potencies against HSV 1, HSV-2, CMV and HIV with ED50's in the range of 0.036 to 2.0 µg/mL. Considering the molecular weights of the enzymatically synthesized melanins in aqueous solution, these new antiviral agents are active at concentrations in the range of 6 to 100 nM. ES-CAM and ES-EM inhibit infections by virus strains that are resistant to typical antiviral medications such as acyclovir and ganciclovir.

The anti-HIV results were determined by the Viral Quality Assurance Laboratory at Rush University directed by James Bremer, Ph.D. The VQA laboratory is responsible for establishing the quality control testing for all AIDS Clinical Trial Group (ATCG) laboratories in the U.S. The results with ES-CAM and ES-EM using a laboratory strain of HIV tested in the VQA laboratory were 0.21 ug/mL and 0.036 ug/mL respectively.

Therefore, the enzymatically synthesized ES-CAM and ES-EM prepared according to this invention will prevent many different viral infections including HSV and HIV by acting as inhibitors of virus binding and/or virus fusion. Melanins that were nonenzymatically synthesized from caffeic acid and esculetin precursors by spontaneous polymerization at a basic pH typically had maximum anti-HSV 1 potencies (ED50) of ≥4 μg/mL. Hence, the antiviral activities of melanins made by the enzymatic synthesis process described here are 2- to 16-fold greater than those of spontaneous polymerized melanins prepared from the same precursors.

ED50 values for the enzymatic and chemically synthesized melanins as determined in our laboratory and the Bremer laboratory at Rush University are summarized in Table 4. BAL HIV-1 strain was used in the HIV assay. The cells were exposed to the compounds for 1 hour prior to infection with the BAL HIV-1 strain (200 TCID50/200,000 cells). The cells (200,000 cells per well) were infected overnight and the next day 100 μL of supernatant was removed and 100 μL of fresh compound media was added to the appropriate wells. At day 4, 125 μL of supernatant was removed and 150 μL of compound media was added. At day 7, the supernatant was diluted 1:1560 and tested using Perkin-Elmer's HIV-1 p24 kit.

TABLE 4

Physical Properties and Antiviral Activities of Synthetic Melanins Prepared Enzymatically (Process 1) and Chemically (Process 2).

| Process | Cmpd | Precursor | % Recovery | Molecular Mass (kDa) | ED50 HSV1 (ug/mL) | ED50 HSV2 (ug/mL) | ED50 hCMV [AD169] (ug/mL) | ED50 hCMV [D16] (ug/mL) | ED50 HIV (ng/mL) | ED50 HIV (nM) |
|---|---|---|---|---|---|---|---|---|---|---|
| 1 | ESCAM | caffeic acid | 85 | 19.7 | 1 | 0.25 | 0.25 | 0.25 | 210 | 10.65 |
| 1 | ESEM | esculetin | 77 | 15.4 | 2 | 1 | 1 | 0.5 | 36 | 2.33 |
| 2 | C1 | pyrogallol | 64 | 8.37 | 32 | 16 | 2.5 | 2.5 | 4.16 | 0.5 |
| 2 | C2 | quercetin dihydrate | 75 | 11.27 | 16 | 8 | 2 | 1 | 21.89 | 1.94 |
| 2 | C3 | daphnetin | 63 | 6.83 | 128 | 64 | 10 | 10 | 17.58 | 2.57 |
| 2 | C4 | 2,3 dihydroxynapthalene | 52 | 5.13 | 32 | 16 | 5 | 2.5 | 21.95 | 4.28 |
| 2 | C5 | 3,4 dihydroxybenzoic acid (protocatechuric acid) | 60 | 7.31 | 32 | 16 | 5 | 5 | 32.83 | 4.49 |
| 2 | C6 | 6,7-dihydroxy-4-coumarinyl acetic acid | 51 | 7.03 | 128 | 32 | 20 | 20 | 39.35 | 5.6 |
| 2 | C7 | baicalein | 11 | 4.59 | 128 | 64 | | | 13.72 | 2.99 |
| 2 | C8 | gallic acid | 48 | 6.45 | >128 | 64 | 40 | 40 | 115.01 | 17.83 |
| 2 | C9 | 3,4 dihydroxyphenylacetic acid | 75 | 15.45 | 4 | 4 | 1 | 1 | 17.55 | 1.14 |
| 2 | C10 | esculetin | 73 | 9.4 | 16 | 4 | 5 | 2.5 | 124.67 | 13.26 |
| 2 | C11 | caffeic acid | 77 | 13.8 | 8 | 8 | 1 | 1 | 17.87 | 1.29 |
| 2 | C12 | catechin | 89 | 80.23 | 4 | 2 | 0.5 | 0.25 | 19.12 | 0.24 |
| 2 | C13 | nordihydroquaiuretic acid | 58 | 14.97 | 32 | 16 | 5 | 5 | 59.39 | 3.97 |
| 2 | C14 | baicalein hydrate | 13 | 4.88 | 128 | 128 | | | 10.4 | 2.13 |
| 2 | C15 | 2,3,4 trihydroxybenzoic acid | 39 | 6.74 | 64 | 16 | 20 | 20 | 8.57 | 1.27 |
| 2 | C16 | epinephrine (bitartrate) | 14 | 6.44 | >128 | 128 | 40 | 20 | 216.38 | 33.6 |
| 2 | C17 | epinine (2 deoxy norepinephrine) | 48 | 99.24 | 4 | 4 | 1 | 1 | 138.09 | 1.39 |
| 2 | C18 | 2,3,4 trihydroxybenzaldehyde | 45 | 9.71 | 32 | 32 | 2 | 2 | 42.12 | 4.34 |

Several of the chemically synthesized compounds, in particular C1, C12, C9, C11 and C17 are highly potent inhibitors of HIV infection in vitro, while the enzymatic synthetic products have the highest in vitro potencies for the inhibition of herpes virus infections.

The enzymatically synthesized melanins ES-CAM and ES-EM and 8 of the chemically synthesize melanins (C1, C2, C4, C9, C11, C12, C15, and C17) were submitted to the National Institute of Allergy and Infectious Diseases (NIAID) Antimicrobial Acquisition and Coordinating Facility (Project Officer Dr. Chris Tseng) to be tested for in vitro activity against 7 Types of herpesviruses; 7 respiratory viruses; 2 orthopoxviruses, and a Biodefense panel of 10 viruses as well as for in vivo activity testing in animal models for herpesviruses, respiratory viruses, and scrapie. The details of the assay protocols used for testing and the investigators that carried out the testing are described on the NIAID website. The results that have been reported to date are presented in Tables 5-14.

The results reported for anti-HSV-1 (Table 5) anti-HSV-2 (Table 6) activities confirmed those obtained in our own laboratory. Note that the EC50's for 5 of the synthetic melanins were less than that of Acyclovir (ACV), the major current antiviral drug currently used to treat HSV-2 infections in humans. Synthetic melanin C2 was more than 20 times as potent as ACV in this assay.

The synthetic melanins demonstrate activity toward a number of respiratory viruses (tables 7-11). Especially significant are the high potencies of 4 of our compounds toward Influenzas A (including H5N1) and B. Since the portals of entry of the respiratory viruses and many other clinically important enveloped viruses are the epithelial surfaces of the oral cavity, the nasopharynx, the respiratory tract (and possibly the GI Tract) and the conjunctiva, antiviral prophylaxis or treatment could be delivered by non parenteral application, such as drops, oral solutions, sprays or nebulized droplets. Given the fact that current human antiviral therapies for H5N1 are prohibited from use in poultry because of the risk of the emergence of resistant strains that might be transmitted to humans, our compounds may be especially valuable in that they have a different mechanism of action than the currently available drugs. The synthetic melanins could be used for veterinary applications, while other drugs like the neuraminidase inhibitor, Oseltamivir, could be reserved for human use.

TABLE 5

Anti-HSV-1 Potency in HFF cells (μg/mL).

| Cmpds | Assay | Cell Line | EC50 | EC90 | CC50 | SI | ACV EC50 | ACV CC50 | GCV CC50 |
|---|---|---|---|---|---|---|---|---|---|
| C1 | CPE | HFF Cells | 8.9 | 45 | >100 | >11 | 1.1 | | |
| | Tox-NRU | Stationary HFF Cells | | | >100 | | | >100 | >100 |
| C2 | CPE | HFF Cells | 2.2 | 13 | >100 | >45 | 1.1 | | |
| | Tox-NRU | Stationary HFF Cells | | | >100 | | | >100 | >100 |
| C4 | CPE | HFF Cells | >100 | >100 | >100 | 0 | 1.1 | | |
| | Tox-NRU | Stationary HFF Cells | | | >100 | | | >100 | >100 |
| C9 | CPE | HFF Cells | 2.6 | >100 | >100 | >38 | 1.1 | | |
| | Tox-NRU | Stationary HFF Cells | | | >100 | | | >100 | >100 |
| C11 | CPE | HFF Cells | 1.9 | 3.4 | >100 | >53 | 1.1 | | |
| | Tox-NRU | Stationary HFF Cells | | | >100 | | | >100 | >100 |
| C12 | CPE | HFF Cells | 2.4 | 4 | >100 | >42 | 1.1 | | |
| | Tox-NRU | Stationary HFF Cells | | | >100 | | | >100 | >100 |
| C15 | CPE | HFF Cells | 25.6 | >100 | >100 | >3.9 | 1.1 | | |
| | Tox-NRU | Stationary HFF Cells | | | >100 | | | >100 | >100 |
| C17 | CPE | HFF Cells | 1.8 | 4.2 | >100 | >56 | 1.1 | | |
| | Tox-NRU | Stationary HFF Cells | | | >100 | | | >100 | >100 |
| ESCAM | CPE | HFF Cells | 1.8 | 3.7 | >100 | >56 | 1.1 | | |
| | Tox-NRU | Stationary HFF Cells | | | >100 | | | >100 | >100 |
| ESEM | CPE | HFF Cells | 1.4 | 2.6 | >100 | >71.4 | 1.1 | | |
| | Tox-NRU | Stationary HFF Cells | | | >100 | | | >100 | >100 |

TABLE 6

Anti-HSV-2 Potency in HFF cells (μg/mL).

| Cmpds | Assay | Cell Line | EC50 | EC90 | CC50 | SI | ACV EC50 | ACV CC50 | GCV CC50 |
|---|---|---|---|---|---|---|---|---|---|
| C1 | CPE | HFF Cells | 0.11 | 10.6 | >100 | >909 | 1.4 | | |
| | Tox-NRU | Stationary HFF Cells | | | >100 | | | >100 | >100 |
| C2 | CPE | HFF Cells | 0.06 | 2.4 | >100 | >1666 | 1.4 | | |
| | Tox-NRU | Stationary HFF Cells | | | >100 | | | >100 | >100 |
| C4 | CPE | HFF Cells | >100 | >100 | >100 | 0 | 1.4 | | |
| | Tox-NRU | Stationary HFF Cells | | | >100 | | | >100 | >100 |
| C9 | CPE | HFF Cells | 0.1 | >100 | >100 | >1000 | 1.4 | | |
| | Tox-NRU | Stationary HFF Cells | | | >100 | | | >100 | >100 |

TABLE 6-continued

Anti-HSV-2 Potency in HFF cells (μg/mL).

| Cmpds | Assay | Cell Line | EC50 | EC90 | CC50 | SI | ACV EC50 | ACV CC50 | GCV CC50 |
|---|---|---|---|---|---|---|---|---|---|
| C11 | CPE | HFF Cells | 0.8 | >100 | >100 | >125 | 1.4 | | |
| | Tox-NRU | Stationary HFF Cells | | | >100 | | | >100 | >100 |
| C12 | CPE | HFF Cells | 0.3 | 14 | >100 | >333 | 1.4 | | |
| | Tox-NRU | Stationary HFF Cells | | | >100 | | | >100 | >100 |
| C15 | CPE | HFF Cells | >100 | >100 | >100 | 0 | 1.4 | | |
| | Tox-NRU | Stationary HFF Cells | | | >100 | | | >100 | >100 |
| C17 | CPE | HFF Cells | 2.8 | 16 | >100 | >36 | 1.4 | | |
| | Tox-NRU | Stationary HFF Cells | | | >100 | | | >100 | >100 |
| ESCAM | CPE | HFF Cells | 4.2 | 20 | >100 | >24 | 1.4 | | |
| | Tox-NRU | Stationary HFF Cells | | | >100 | | | >100 | >100 |
| ESEM | CPE | HFF Cells | 11.4 | 31 | >100 | >8.7 | 1.4 | | |
| | Tox-NRU | Stationary HFF Cells | | | >100 | | | >100 | >100 |

TABLE 7

Anti-viral Potency (μg/mL).

| | EC50's | | | | | | | |
|---|---|---|---|---|---|---|---|---|
| CMPD | Flu A H1N1 | Flu A H3N2 | Flu A H5N1 | Flu B | SARS | Vaccinia | Cowpox | Yellow Fever |
| C1 | 32 | 21 | 25 | 32 | 69 | >100 | >100 | >100 |
| C2 | 73 | 56 | 32 | 32 | >100 | 90.2 | 72.7 | >100 |
| C4 | 56 | 56 | 5.6 | 32 | 13 | >100 | 75.8 | >100 |
| C9 | 46 | 35 | 22 | 32 | 57 | 63.1 | 35.1 | >100 |
| C11 | 32 | 56 | 8.3 | 32 | 32 | 80.3 | >100 | >100 |
| C12 | 2.5 | 3.6 | * | * | 27 | 10.4 | 26.3 | >100 |
| C15 | 32 | >100 | 36 | >100 | >100 | >100 | >100 | >100 |
| C17 | 19 | 4.8 | * | 32 | 25 | 11.7 | 26.8 | >100 |
| ESCAM | 11 | 3.2 | * | * | 25 | 17.5 | 35.8 | >100 |
| ESEM | 2.5 | * | * | 5 | 32 | 16.9 | 27.6 | >100 |

* Compound demonstrated moderate to high activity in screening assay. See additional test results in Table 8, 9, 10, and 11.

TABLE 8

Anti-viral Potency of C12.

| Virus | Virus Strain | Assay | Trial No. | EC50 | EC90 | IC50 | SI |
|---|---|---|---|---|---|---|---|
| Flu A (H5N1) | Duck/MN/1525/81 | Neutral Red | 1 | 0.84 | | >100 | >120 |
| | | Visual | 1 | 0.75 | | 100 | 130 |
| | | Virus Yield | 2 | | 3.2 | | 31 |
| | | Visual-CONF | 2 | 0.75 | | 100 | 130 |
| | Vietnam/1203/2004H | Neutral Red | 1 | 3 | | >100 | >33 |
| | | Visual | 1 | 3.2 | | 32 | 10 |
| | | Neutral Red | 2 | 0.83 | | >100 | >120 |
| | | Visual | 2 | 0.59 | | 53 | 90 |
| | | Virus Yield | 3 | | 6.2 | | 8.5 |
| | | Visual-CONF | 3 | 0.59 | | 53 | 90 |
| Flu B | Malaysia/2506/2004 | Neutral Red | 1 | 4.9 | | >100 | >20 |
| | | Visual | 1 | 4.6 | | 32 | 7 |
| | | Neutral Red | 2 | 2.8 | | >100 | >36 |
| | | Visual | 2 | 2 | | >100 | >50 |
| | | Virus Yield | 3 | | 30 | | >3.3 |
| | | Visual-CONF | 3 | 2 | | >100 | >50 |

(Cell line: MDCK. Vehicle: Sponsor Buffer. Unit: μg/mL).

TABLE 9

Anti-viral Potency of C17.

| Virus | Virus Strain | Assay | Trial No. | EC50 | EC90 | IC50 | SI |
|---|---|---|---|---|---|---|---|
| Flu A (H5N1) | Duck/MN/1525/81 | Neutral Red | 1 | 2.3 | | >100 | >43 |
| | | Visual | 1 | 2.8 | | >100 | >36 |
| | | Virus Yield | 2 | | 6.3 | | >16 |
| | | Visual-CONF | 2 | 2.8 | | >100 | >36 |
| | Vietnam/1203/2004H | Neutral Red | 1 | 6.2 | | >100 | >16 |
| | | Visual | 1 | 0.83 | | 100 | 120 |

(Cell line: MDCK. Vehicle: Sponsor Buffer. Unit: μg/mL).

TABLE 10

Anti-viral Potency of ES-EM.

| Virus | Virus Strain | Assay | Trial No. | EC50 | EC90 | IC50 | SI |
|---|---|---|---|---|---|---|---|
| Flu A (H5NI) | Duck/MN/1525/81 | Neutral Red | 1 | 0.23 | | 96 | 420 |
| | | Visual | 1 | 0.19 | | 53 | 280 |
| | | Virus Yield | 2 | | 1.9 | | 28 |
| | | Visual-CONF | 2 | 0.19 | | 53 | 280 |
| | Vietnam/1203/2004H | Neutral Red | 1 | 3.1 | | 34 | 11 |
| | | Visual | 1 | 1.8 | | 46 | 26 |
| | | Neutral Red | 2 | 0.51 | | >100 | >200 |

TABLE 10-continued

Anti-viral Potency of ES-EM.

| Virus | Virus Strain | Assay | Trial No. | EC50 | EC90 | IC50 | SI |
|---|---|---|---|---|---|---|---|
| | | Visual | 2 | 0.21 | | 65 | 310 |
| | | Virus Yield | 3 | | 1.5 | | 43 |
| | | Visual-CONF | 3 | 0.21 | | 65 | 310 |

(Cell line: MDCK. Vehicle: Sponsor Buffer. Unit: µg/mL).

TABLE 11

Anti-viral Potency of ES-CAM.

| Virus | Vehicle | Assay | Trial No. | EC50 | EC90 | IC50 | SI |
|---|---|---|---|---|---|---|---|
| Flu A (H3N2) | DMSO | Neutral Red | 2 | 9.1 | | >100 | >11 |
| | | Visual | 2 | 6.8 | | >100 | >15 |
| | | Virus Yield | 3 | | 14.5 | | 6.9 |
| | | Visual-CONF | 3 | 6.8 | | >100 | >15 |
| Flu A (H5N1) | Sponsor buffer | Neutral Red | 1 | 4.2 | | 50 | 12 |
| | | Visual | 1 | 4.3 | | >100 | >23 |
| | | Virus Yield | 2 | | 4.4 | | >23 |
| | | Visual-CONF | 2 | 4.3 | | >100 | >23 |
| | | Neutral Red | 2 | 3.1 | | >100 | >32 |
| | | Visual | 2 | 1.8 | | 53 | 29 |
| Flu B | | Neutral Red | 1 | 3.4 | | 79 | 23 |
| | | Visual | 1 | 3.2 | | 40 | 13 |
| | | Neutral Red | 2 | 5.9 | | >100 | >17 |
| | | Visual | 2 | 6 | | >100 | >17 |
| | | Virus Yield | 3 | | 7.2 | | >14 |
| | | Visual-CONF | 3 | 6 | | >100 | >17 |

(Cell line: MDCK; Unit: µg/mL).

TABLE 12

Anti-viral Potency.

EC50's (ug/mL)

| CMPD | Adeno | PIV | Rhino | RSV A | Rift Valley | Tacaribe | Dengue C |
|---|---|---|---|---|---|---|---|
| C1 | >100 | >100 | >100 | >100 | >100 | >100 | nt |
| C2 | >100 | >100 | >100 | >100 | >100 | >100 | 33 |
| C4 | >100 | >100 | >100 | >100 | >100 | >100 | 26 |
| C9 | >100 | >100 | >100 | >100 | 42 | >100 | >100 |
| C11 | >100 | >100 | >100 | >100 | 64 | >100 | >100 |
| C12 | >100 | >100 | >100 | 32 | 30 | >100 | >100 |
| C15 | >100 | >100 | >100 | >100 | >100 | >100 | nt |
| C17 | >100 | >100 | >100 | 38 | 28 | nt | nt |
| ESCAM | >100 | >100 | >100 | 41 | 32 | 45 | nt |
| ESEM | >100 | >100 | >100 | >100 | 30 | 41 | nt | nt: Compound not tested

The potency and the cytotoxicity of melanins in the present invention were also evaluated for other viruses (VZV, EBV) in various cell lines, shown in table 13 and 14. ESEM, C2, C9 and C12 have high potencies against VZV with EC50's in the range of 0.03 to 3.9 µg/mL. The potencies of ES-EM and C12 exceeded that of Acyclovir (AVC), the positive control that was used in the assay. Cytotoxicity study showed all of these four melanins have CC50's larger than 100 µg/mL. None of the compounds tested had significant in vitro activity against EBV.

TABLE 13

Anti-Viral Potency in HFF cells (µg/mL).

| | VZV (Varicella Zoster Virus) | | | | ACV |
|---|---|---|---|---|---|
| Cmpd | EC50 | EC90 | CC50 | SI | EC50 |
| ESCAM | nt | nt | nt | nt | 0.06 |
| ESEM | <0.0300 | <0.0300 | >100 | >3333 | 0.06 |
| C1 | 36 | 49.3 | >100 | >2.8 | 0.17 |
| C2 | 3.9 | 31.7 | >100 | >26 | 0.17 |
| C4 | 10 | 43.4 | >100 | >10 | 0.17 |
| C9 | 3.7 | >100 | >100 | >27 | 0.17 |
| C11 | 64.8 | 95.7 | >100 | >1.5 | 0.06 |
| C12 | <0.0300 | <0.0300 | >100 | >3333 | 0.06 |
| C17 | nt | nt | nt | nt | 0.06 | nt: Compound not tested.

TABLE 14

Anti-Viral Potency in Akata cells (µg/mL).

| | EBV (Epstein-Barr Virus) | | | | |
|---|---|---|---|---|---|
| Cmpd | EC50 | EC90 | CC50 | SI | ACV EC50 |
| ESCAM | 98.3 | >100 | >100 | >1 | 2.7 |
| ESEM | >100 | >100 | >100 | 0 | 2.7 |
| C1 | >100 | >100 | >100 | 0 | 0.7 |
| C2 | >100 | >100 | >100 | 0 | 0.7 |
| C4 | >100 | >100 | >100 | 0 | 0.7 |
| C9 | >20 | >20 | >20 | 0 | 0.7 |
| C11 | >20 | >20 | >20 | 0 | 0.7 |
| C12 | >100 | >100 | >100 | 0 | 0.7 |
| C15 | >100 | >100 | >100 | 0 | 0.7 |
| C17 | >100 | >100 | >100 | 0 | 0.7 |

Inhibition of Lysozyme Fibrillation by Enzymatically and Chemically Synthesized Melanins.

The inhibition of lysozyme fibrillation in vitro was tested with synthetic and natural melanins.

Figure 8:
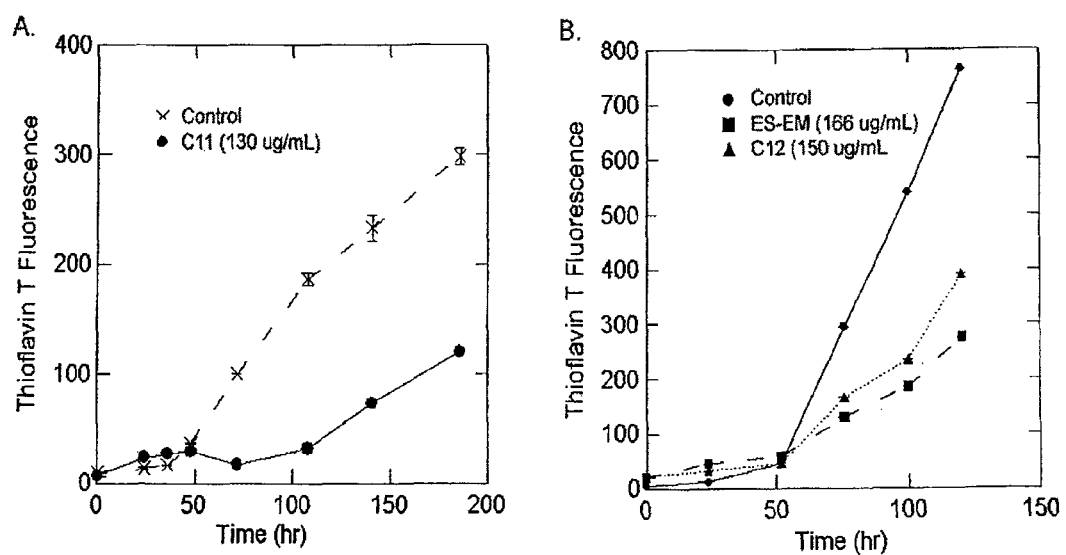
FIG. 8 illustrates the effect of the synthetic melanins ES-EM, C11, and C12 on Lysozyme Fibrillation in vitro.

Solutions of lysozyme (hen egg white, 20 mg/mL) were incubated in 20 mM glycine-HCl buffer at 58° C. for 8 days in the presence of one of the melanins. The incubation mixtures were sampled repeatedly and the kinetics of lysozyme fibrillation were evaluated by Thioflavin T (Tht) fluorescence, native PAGE, and fluorescence and dark field microscopy. Compounds C11, ES-EM, and C12 (FIG. 8) inhibited the development of THT fluorescence to levels that were 16%, 42%, and 61%, respectively, of untreated control mixtures. PAGE analysis of the time points taken during the incubation containing C11 showed that this compound decreased the generation of lysozyme oligomers during the first 48 hours of incubation and delayed the progression of the assembly of lysozyme monomers and oligomers into lysozyme fibers and aggregates. The data suggests that synthetic melanins may be of therapeutic value as fibrillogenesis inhibitors.

It is intended that the foregoing detailed description be regarded as illustrative rather than limiting, and that it be understood that it is the following claims, including all equivalents, that are intended to define the spirit and scope of this invention.

The invention claimed is:

1. A method for producing a water soluble bioactive melanin polymer, the method comprising:

treating a substrate containing at least two hydroxyl groups with a metal-containing catalyst, in the presence of oxygen, for a time sufficient to produce quinones; and polymerizing the quinones to yield a water soluble, bioactive melanin polymer; wherein the substrate is selected from the group consisting of cinnamic acids, coumarins, phenols, hydroxyflavanones, hydroxynapthalenes, hydroxybenzoic acids, flavonoids, pyrocatechols, hydroxybenzaldehydes, and combinations thereof.

2. The method of claim 1, wherein the substrate is in an aqueous solution.

3. The method of claim 2, wherein the aqueous solution has a basic pH.

4. The method of claim 2, wherein the aqueous solution is a sodium carbonate buffer at a pH of about 10.6.

5. The method of claim 1, wherein the metal-containing catalyst is selected from the group consisting of an iron complex, a cobalt complex, a nickel complex, and salcomine.

6. The method of claim 1, wherein the substrate is selected from the group consisting of alizarin, pyrogallol, quercetin dehydrate, daphnetin, 2,3-dihydroxynapthalene, 3,4-dihydroxybenzoic acid (protocatechuric acid), 6,7-dihydroxy-4-coumarinyl acetic acid, baicalein, gallic acid, 3,4-dihydroxyphenylacetic acid, esculetin, caffeic acid, catechin, nordihydroquaiuretic acid, baicalein hydrate, 2,3,4-trihydroxybenzoic acid, epinephrine (bitartrate), epinine (2-deoxy norepinephrine), 2,3,4-trihydroxybenzaldehyde, and combinations thereof.

7. The method of claim 1, further comprising:
purifying the melanin polymer.

8. The method of claim 1, wherein the metal-containing catalyst is a polyphenol oxidase and the substrate is treated with the polyphenol oxidase in an aqueous buffer at a pH of about 7.0 for a time sufficient to produce the quinones.

9. The method of claim 8, further comprising inactivating the polyphenol oxidase.

* * * * *